US011421017B2

(12) United States Patent
Kwon et al.

(10) Patent No.: US 11,421,017 B2
(45) Date of Patent: Aug. 23, 2022

(54) RECOMBINANT HERPES SIMPLEX VIRUS HAVING EXPRESSION CASSETTE EXPRESSING FUSED PROTEIN OF CANCER CELL-TARGETING DOMAIN AND EXTRACELLULAR DOMAIN OF HVEM AND USE THEREOF

(71) Applicants: Gencellmed Inc., Seoul (KR); KOREA INSTITUTE OF RADIOLOGICAL & MEDICAL SCIENCES, Seoul (KR)

(72) Inventors: Heechung Kwon, Gyeonggi-do (KR); Hyunjung Baek, Gyeonggi-do (KR); Hyun Yoo Joo, Seoul (KR)

(73) Assignees: GENCELLMED INC., Seoul (KR); KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 139 days.

(21) Appl. No.: 16/999,158

(22) Filed: Aug. 21, 2020

(65) Prior Publication Data

US 2021/0054052 A1 Feb. 25, 2021

(30) Foreign Application Priority Data

Aug. 22, 2019 (KR) ........................ 10-2019-0103317
Jun. 16, 2020 (KR) ........................ 10-2020-0072978

(51) Int. Cl.

| | |
|---|---|
| ***C07K 16/08*** | (2006.01) |
| ***A61K 39/00*** | (2006.01) |
| ***A61K 39/245*** | (2006.01) |
| ***A61K 47/65*** | (2017.01) |

(52) U.S. Cl.

CPC ...... *C07K 16/087* (2013.01); *A61K 39/00114* (2018.08); *A61K 39/001106* (2018.08); *A61K 39/001109* (2018.08); *A61K 39/001128* (2018.08); *A61K 39/001129* (2018.08); *A61K 39/245* (2013.01); *A61K 47/65* (2017.08); *A61K 2039/55527* (2013.01); *C07K 2317/622* (2013.01); *C07K 2319/33* (2013.01)

(58) Field of Classification Search

CPC ............ C07K 16/087; C07K 2317/622; C07K 2319/33; C07K 16/32; C07K 16/3007; C07K 2317/14; C07K 14/70578; C07K 16/30; C07K 2319/30; C07K 14/005; A61K 39/001106; A61K 39/001109; A61K 39/001128; A61K 39/001129; A61K 39/00114; A61K 39/245; A61K 47/65; A61K 2039/55527; A61K 35/763; Y02A 50/30; C12N 2710/16632; C12N 2710/16643; C12N 15/86; C12N 7/00; C12N 2710/16032; C12N 2710/16011; A61P 35/00

See application file for complete search history.

(56) References Cited

U.S. PATENT DOCUMENTS

| | | | | |
|---|---|---|---|---|
| 2010/0233758 | A1 | 9/2010 | Kwon et al. | |
| 2013/0096186 | A1 * | 4/2013 | Glorioso, III .. | A61K 39/001159 435/320.1 |
| 2018/0002723 | A1 * | 1/2018 | Campadelli .......... | C12N 15/869 |
| 2021/0046130 | A1 * | 2/2021 | Jia .......................... | A61K 35/76 |

FOREIGN PATENT DOCUMENTS

KR 10-2009-0028971 A 3/2009

OTHER PUBLICATIONS

Fan Q, Kopp S, Connolly SA, Muller WJ, Longnecker R. Mapping sites of herpes simplex virus type 1 glycoprotein D that permit insertions and impact gD and gB receptors usage. Sci Rep. Mar. 3, 2017;7:43712. (Year: 2017).*
Menotti L, Nicoletti G, Gatta V, Croci S, Landuzzi L, De Giovanni C, Nanni P, et. al. Inhibition of human tumor growth in mice by an oncolytic herpes simplex virus designed to target solely HER-2-positive cells. Proc Natl Acad Sci U S A. Jun. 2, 2009;106(22):9039-44. Epub May 20, 2009. (Year: 2009).*
Notice of Allowance from corresponding Korean Patent Application No. 10-2021-0117612, dated May 24, 2022.
Menotti, L., et al.; "HSV as a Platform for the Generation of Retargeted, Armed, and Reporter-Expressing Oncolytic Viruses", Viruses, 2018, 10, 352, pp. 1-29.
Baek, H., et al.; "Bispecific Adapter-Mediated Retargeting of a Receptor-Restricted HSV-1 Vector to CEA-Bearing Tumor Cells", Molecular Therapy, 2011, vol. 19 No. 3, 507-514.

* cited by examiner

*Primary Examiner* — Rachel B Gill
(74) *Attorney, Agent, or Firm* — Harness, Dickey & Pierce, P.L.C.

(57) ABSTRACT

The present invention relates to a recombinant herpes simplex virus (HSV) containing an expression cassette capable of expressing a fused protein of a cancer-cell-targeting domain and an extracellular domain of HVEM and the use thereof. When the recombinant HSV infects and enters target cells, which are cancer cells, HSV proliferates, and an adapter, which is the fused protein, is expressed in the cells and is released to the outside of the cells along with the proliferated HSV virion upon cell lysis, or is released even before the virion is released due to cell lysis when the adapter contains a leader sequence, and the fused protein released to the outside of the cells acts to induce the HSV virion to infect surrounding cancer cells expressing a target molecule recognized by the cancer-cell-targeting domain or to increase the infection efficiency thereof.

18 Claims, 10 Drawing Sheets

Specification includes a Sequence Listing.

RECOMBINANT HERPES SIMPLEX VIRUS HAVING EXPRESSION CASSETTE EXPRESSING FUSED PROTEIN OF CANCER CELL-TARGETING DOMAIN AND EXTRACELLULAR DOMAIN OF HVEM AND USE THEREOF

CROSS-REFERENCE TO RELATED APPLICATIONS

This application claims the benefit of and priority to Korean Patent Application Nos. 10-2019-0103317, filed on Aug. 22, 2019 and 10-2020-0072978, filed on Jun. 16, 2020. The entire disclosures of the applications identified in this paragraph are incorporated herein by references.

FIELD

The present invention relates to a recombinant herpes simplex virus having an expression cassette capable of expressing a fused protein of a cancer cell-targeting domain and an extracellular domain of HVEM and the use thereof.

BACKGROUND

In the treatment of cancer, surgical therapy, anti-cancer chemotherapy, radiotherapy and the like have been widely used to date, but most of these have side effects, incomplete treatment effects, and problems such as cancer recurrence and metastasis. Therefore, the development of new and effective cancer therapies is continually required, and in recent years, rapid advancement has been made in anti-cancer immunotherapy such as oncolytic virus, chimeric antigen receptor T (CAR-T) cell therapy and the like.

In anti-cancer immunotherapy, the oncolytic virus is a virus having the characteristic of lysing cancer cells through manipulation of the gene of a living virus and selective proliferation thereof in cancer cells, and is limited in proliferation in normal cells. The virus released by lysis of cancer cells is able to continuously infect surrounding cancer cells, thereby providing a continuous and synergistic therapeutic effect. Moreover, the oncolytic virus is capable of increasing the anti-cancer effect by stimulating the immune response of the human body by releasing an immunogenic tumor antigen in the process of lysing cancer cells. Furthermore, such anti-cancer effects may be enhanced through artificial manipulation so as to express cytokines, chemokines, and the like.

Currently developed oncolytic viruses may be classified into 10 or more types, including adenovirus, herpes simplex virus (HSV), vaccinia virus, etc. Among these, HSV is an enveloped icosahedral virion containing linear double-stranded DNA having a size of 152 kb, and is divided into HSV-1 and HSV-2 types. HSV has many non-essential genes, and the genome size thereof is large, making it easy to manipulate or transport external genes, and the replication cycle thereof is short, and moreover, HSV has high infection efficiency, and is desirably capable of exhibiting improved cancer-cell-targeting efficiency through easy manipulation of glycoproteins involved in cell attachment and infection.

T-VEC (talimogene laherparepvec, product name: Imlygic), approved by the US FDA in October 2015, is an anti-cancer drug (oncolytic virus therapeutic agent) for malignant melanoma using HSV-1. T-VEC is an attenuated HSV-1 virus in which ICP34.5 and ICP47 genes are deleted to attenuate pathogenicity and which expresses GM-CSF (granulocyte-macrophage-colony-stimulating factor) to promote the human immune response. However, T-VEC has a limitation in that the therapeutic efficacy thereof is low due to limited viral proliferation attributed to the loss of some genes.

HSV is a virus having an envelope, and the cell entry of HSV is achieved through complex interactions of gD, gB, gH/gL and gC glycoproteins present in the envelope. First, when gB and gC are attached to 3-O—S HS (3-O-sulfated heparan sulfate) on the cell surface, gD binds to at least one of cell receptors such as HVEM (herpesvirus entry mediator, HveA), nectin-1 (HveC), and nectin-2 (HveB) to thus induce fusion between the virus and the cell membrane, whereby HSV enters the cells (Hiroaki Uchida et al., Generation of Herpesvirus Entry Mediator (HVEM)-restricted Herpes Simplex Virus Type 1 Mutant Viruses: Resistance of HVEM-expressing Cells and Identification of Mutations That Rescue nectin-1 Recognition. J. Virol. 2009 April; 83(7): 2951-61).

Among the cell receptors of HSV, HVEM belongs to the tumor necrosis factor receptor protein family (TNFR family) and is mainly expressed in T/B lymphocytes, macrophages and DC cells, sensory neuron and mucosal epithelial cell (Shui J. W., Kronenberg M. 2013. Gut Microbes 4(2):146-151), but is known to be expressed in abundance in various tumor tissues such as B/T lymphoma, melanoma, colorectal cancer, hepatocellular carcinoma, breast cancer, ovarian serous adenocarcinoma, clear renal cell carcinoma and glioblastoma (Pasero C. et al., Curr. Opin. Pharmacol. 2012. 2(4):478-85, Malissen N. et al., ONCOIMMUNOLOGY 2019, VOL. 8(12):e1665976). HVEM has four CRDs (cysteine-rich domains), which are the feature of the TNFR family, and two of four CRDs are linked with gD of HSV to thus induce the cell entry of HSV-1 and HSV-2 (Sarah A Connolly et al., Structure-based Analysis of the Herpes Simplex Virus Glycoprotein D Binding Site Present on Herpesvirus Entry Mediator HveA (HVEM). J. Virol. 2002 November; 76(21):10894-904).

As already reported by the present inventors, a bispecific fused protein (CEAscFv-HveA) of scFv (single-chain variable fragment) for CEA (carcinoembryonic antigen) and an extracellular domain of HVEM, which is one of the HSV cell surface receptors, is manufactured, and when a cell line expressing CEA is treated with the bispecific fused protein and HSV, the fused protein acts as an adapter to induce HSV to target and infect the corresponding cell line (Korean Patent No. 10-0937774 and U.S. Pat. No. 8,318,662).

When the gene encoding the fused protein (CEAscFv-HveA) serving as the adapter is expressively inserted into the HSV genome so that the fused protein is expressed in cells infected with HSV, it is ascertained that the fused protein acts to induce HSV to thus target and infect the cell line expressing CEA and also that a fused protein (HER2scFv-HveA) of scFv for HER2 (human epidermal growth factor receptor 2), rather than scFv for CEA, and an extracellular domain of HVEM equally induce targeting and infection of a cell line expressing HER2, thus culminating in the present invention.

SUMMARY

Disclosed herein is a recombinant HSV containing an expression cassette capable of expressing an adapter that is a fused protein of a cancer-cell-targeting domain and an extracellular domain of HVEM.

In addition, disclosed herein is a pharmaceutical composition for anti-cancer treatment, comprising the above-mentioned recombinant HSV as an active ingredient.

In addition, disclosed herein is a method of treating or preventing cancer (tumors), including administering a pharmaceutical composition containing the above-mentioned recombinant HSV to a subject such as a patient in an effective amount.

The other or specific aspects of the present invention will be provided below.

The present invention pertains to a recombinant HSV (herpes simplex virus) capable of expressing an adapter, which is a fused protein of a cancer-cell-targeting domain (which may be used interchangeably with a cancer-targeting domain herein, or may be represented as a ligand depending on the context of the present specification) and an extracellular domain of HVEM.

When the recombinant HSV of the present invention infects target cells, which are cancer cells, and enters the target cells, HSV proliferates, and an adapter, which is the fused protein, is expressed in the cells and is released to the outside of the cells along with the proliferated HSV virion upon cell lysis, or is continuously released even before the virion is released due to cell lysis when the adapter contains a leader sequence. The adapter released to the outside of the cells acts to induce the HSV virion to thus infect surrounding cancer cells expressing a target molecule recognized by the cancer-cell-targeting domain of the adapter or to increase the infection efficiency thereof.

In general, a recombinant HSV is HSV that is genetically manipulated so as to be capable of losing or altering certain functions or expressing a target protein of interest by introducing an artificial mutation (through deletion, substitution or insertion of some nucleic acid sequences) compared to a wild-type HSV. In the present invention, a recombinant HSV is HSV capable of expressing an adapter in cancer cells infected therewith by introducing (i.e. inserting) an adapter-expressing cassette (i.e. a construct in which the adapter gene is operably linked with a promoter sequence that enables expression thereof and a polyadenylation signal sequence) into the HSV genome without inhibiting the proliferation of HSV. Recombinant virus production techniques such as genetic manipulation of viruses and production of virions are well known in the art, and reference may be made to the paper [Sandri-Goldin R M et al., Alpha Herpesviruses: Molecular and Cellular Biology, Caister Academic Press, 2006], the paper [Robin H Lachmann, Herpes simplex virus-based vectors, Int J Exp Pathol. 2004 August; 85(4): 177-190], etc. All documents cited in the present specification, including the above documents, are considered part of the present specification.

In particular, in addition to being manipulated to express the adapter, the recombinant HSV of the present invention may be further manipulated to enter the cells only through an HVEM receptor as an entry receptor, rather than nectin-1. In the following examples of the present invention, the sequence of the HSV envelope glycoprotein gD is manipulated to allow HSV to enter the cells only through the HVEM receptor. Specifically, arginine (R) at position 222 of gD and phenylalanine (F) at position 223 of gD are substituted with asparagine (N) and isoleucine (I), respectively, so the function of gD is altered. The recombinant HSV having the gD function thus altered may enter host cells only through the HVEM (HveA) receptor (Hiroaki Uchida et al. Generation of Herpesvirus Entry Mediator (HVEM)-restricted Herpes Simplex Virus Type 1 Mutant Viruses: Resistance of HVEM-expressing Cells and Identification of Mutations That Rescue nectin-1 Recognition. J. Virol. 2009 April; 83(7):2951-61). The HVEM (HveA) receptor is known to be expressed in abundance in various tumor tissues such as BIT lymphoma and melanoma (Pasero C. et al., Curr. Opin. Pharmacol. 2012. 2(4):478-85, Malissen N. et al., ONCOIMMUNOLOGY 2019, VOL. 8(12): e1665976).

Moreover, the recombinant HSV of the present invention may be mutated so that non-essential genes that are not required for the proliferation of HSV (i.e. survival and replication) are deleted or the function thereof is not exhibited (i.e. transcription or translation is interrupted). Specific examples of the non-essential genes may include UL3 gene (e.g. GenBank Accession No. AFE62830.1), UL4 gene (e.g. GenBank Accession No. AFE62831.1), UL14 gene (e.g. GenBank Accession No. AFE62841.1), UL16 gene (e.g. GenBank Accession No. AFE62843.1), UL21 gene (e.g. GenBank Accession No. AFE62848.1), UL24 gene (e.g. GenBank Accession No. AFE62851.1), UL31 gene (e.g. GenBank Accession No. AFE62859.1), UL32 gene (e.g. GenBank Accession No. AFE62860.1), US3 gene (e.g. GenBank Accession No. AFE62891.1), UL51 gene (e.g. GenBank Accession No. AFE62880.1), UL55 gene (e.g. GenBank Accession No. AFE62884.1), UL56 gene (e.g. GenBank Accession No. AFE62885.1), US2 gene (e.g. GenBank Accession No. AFE62890.1), US12 gene (e.g. GenBank Accession No. AFE62901.1; ICP47 gene), LAT gene (e.g. GenBank Accession No. JQ673480.1), gB gene (e.g. sequence between 52996 and 55710 of GenBank Accession No. GU734771.1), gL gene (e.g. GenBank Accession No. AFE62828.1), gH gene (e.g. GenBank Accession No. AFE62849.1), gD gene (e.g. GenBank Accession No. AFE62894.1), and the like.

For more specific information on the non-essential genes of HSV, reference may be made to the paper [D M Knipe and P M Howley (eds.) Fields virology (vol. 2) Lippincott Williams & Wilkins, Philadelphia, Pa. 2001. pp. 2399-2460)], the paper [Subak-Sharpe J. H., Dargan D. J. HSV molecular biology: general aspects of herpes simplex virus molecular biology Virus Genes, 1998, 16(3): 239-251], the paper [Travis J. Taylor and David M. Knipe, Proteomics of Herpes Simplex Virus Replication Compartments: Association of Cellular DNA Replication, Repair, Recombination, and Chromatin-Remodeling Proteins with ICP8, J. Virol. 2004 June; 78(11): 5856-5866], and the like.

The recombinant HSV of the present invention may be a recombinant HSV-1 virus, a recombinant HSV-2 virus, or an HSV-1/HSV-2 chimeric virus (i.e. a recombinant HSV in which the genome contains both DNA derived from HSV-1 and DNA derived from HSV-2), preferably a recombinant HSV-1 virus, and more preferably a recombinant HSV-1 derived from an HSV-1 KOS strain. The HSV-1 KOS strain is available from ATCC (Cat No VR-1493™), and the entire genome sequence of the strain is completely analyzed and represented in GenBank Accession No. JQ673480.1 (Stuart J. Macdonald et al. Genome Sequence of Herpes Simplex Virus 1 Strain KOS. J. Virol. 2012 June; 86(11):6371-2).

The genome of the HSV-1 virus is composed of 152 kb double-stranded linear DNA encoding a total of 84 genes, comprising two fragments connected to each other, namely a long fragment (L region) and a short fragment (S region). The long fragment (L region) accounts for about 82% of the genome, and the short fragment (S region) accounts for about 18% of the genome, and the long and short fragments are joined by two IRLs (intermediate inverted repeat sequences), which are junction regions, and TRL (terminal inverted repeat segment) is present at the end of each fragment. The L region (UL) comprises 56 UL1-UL56 genes and 10 genes (UL8.5, 9.5, 10.5, 12.5, 15.5, 20.5, 26.5, 27.5, 43.5, 49.5), the S region (US) comprises 12 US1-US12 and 2 genes (US1.5, 8.5), and two IRLs, which are junction regions, comprise 4 genes (ICP4, ICP34.5, ICP0 and LAT).

In the present invention, the adapter-expressing cassette is configured such that the adapter gene is operably linked with a promoter sequence that enables expression thereof and a polyadenylation signal sequence that is a transcription termination signal sequence. Here, "operably linked" means a linkage that enables transcription and/or translation of the expressed adapter gene. For example, when any promoter affects the transcription of the adapter gene linked thereto, the promoter is operably linked to the adapter gene.

Typically, a promoter is a nucleic acid sequence having a function of controlling transcription of one or more genes, which is located at the upstream (5' side) of the transcription start site of a gene and includes a binding site to a DNA-dependent RNA polymerase, a transcription start site, a transcription-factor-binding site, and the like. In the case of eukaryotic origin, the promoter includes a TATA box upstream of the transcription start site (normally located at positions −20 to −30 with respect to the transcription start site (+1)), a CAAT box (usually located at position −75 with respect to the transcription start site), an enhancer, a transcription-factor-binding site, and the like.

So long as the promoter is able to express a target gene linked thereto, all of a constitutive promoter (which induces gene expression at all times), an inducible promoter (which induces expression of a target gene in response to a specific external stimulus), a tissue-specific promoter (which induces gene expression in specific tissues or cells), a tissue-nonspecific promoter (which induces gene expression in all tissues or cells), an endogenous promoter (which is derived from virus-infected cells), and an exogenous promoter (which is derived from cells other than virus-infected cells) may be used. Many promoters are known in the art, among which an appropriate promoter may be selectively used. For example, useful are a CMV (cytomegalovirus) promoter, a RSV (Rous sarcoma virus) promoter, an HSV (herpes simplex virus) TK (thymidine kinase) promoter, an adenovirus late promoter, a vaccinia virus 75K promoter, an SV40 promoter, a metallothionein promoter, a CD45 promoter (hematopoietic-stem-cell-specific promoter), a CD14 promoter (monocyte-specific promoter), and a cancer-cell-specific promoter (tumor specific promoter) such as Survivin, Midkine, TERT, CXCR4, etc. In particular, when a cancer-cell-specific promoter is used, the expression of the adapter is induced only in the cancer cells, thus suppressing adapter expression in normal cells, thereby increasing the safety of the recombinant HSV of the present invention.

The adapter-expressing cassette is configured to include a transcription termination signal sequence in addition to the promoter, and the transcription termination signal sequence is a sequence that acts as a poly(A) addition signal (polyadenylation signal) to increase the integrity and efficiency of transcription. Many transcription termination signal sequences are known in the art, among which an appropriate sequence, such as an SV40 transcription termination signal sequence, an HSV TK (herpes simplex virus thymidine kinase) transcription termination signal sequence, or the like, may be selectively used.

The adapter-expressing cassette is expressively inserted into the HSV genome without inhibiting the proliferation of HSV, and such insertion may be carried out without deletion of the HSV genome, or insertion into loci from which some or all of non-essential genes in the HSV genome are deleted may be conducted. When the adapter-expressing cassette is inserted without deletion of the HSV genome, it may be inserted between genes. Preferred examples of the insertion locus include the locus between UL3 and UL4 genes, the locus between UL26 and UL27 genes, the locus between UL37 and UL38 genes, the locus between UL48 and UL49 genes, the locus between UL53 and UL54 genes, the locus between US1 and US2 genes, etc.

When the adapter-expressing cassette is inserted into loci from which some or all of the non-essential genes in the HSV genome are deleted, the deleted non-essential genes may be any non-essential genes as exemplified above.

In the recombinant HSV of the present invention, the cancer-cell-targeting domain of the adapter is a site that specifically recognizes and binds to the target molecule of cancer cells, which are target cells, and the target molecule recognized by the cancer-cell-targeting domain is any antigen or any receptor present on the surface of cancer cells.

The antigen or receptor is preferably an antigen or receptor that is expressed only in cancer cells or is overexpressed in cancer cells compared to normal cells. Examples of the antigen or receptor may include target molecules, such as EGFRvIII (epidermal growth factor receptor variant III) expressed in glioblastoma, EGFR (epidermal growth factor receptor) overexpressed in anaplastic thyroid cancer, breast cancer, lung cancer, glioma and the like, a metastin receptor overexpressed in papillary thyroid cancer and the like, an ErbB-based receptor tyrosine kinase overexpressed in breast cancer and the like, HER2 (human epidermal growth factor receptor 2) overexpressed in breast cancer, bladder cancer, gallbladder cancer, cholangiocarcinoma, esophagogastric junction cancer and the like, a tyrosine kinase-18-receptor (c-Kit) overexpressed in sarcomatoid renal carcinoma and the like, an HGF receptor c-Met overexpressed in esophageal adenocarcinoma and the like, CXCR4 or CCR7 overexpressed in breast cancer and the like, an endothelin-A receptor overexpressed in prostate cancer, PPAR-δ (peroxisome proliferator activated receptor δ) overexpressed in rectal cancer and the like, PDGFR-α (platelet-derived growth factor receptor α) overexpressed in ovarian cancer and the like, CD133 overexpressed in liver cancer, multiple myeloma and the like, CEA (carcinoembryonic antigen) overexpressed in lung cancer, colorectal cancer, stomach cancer, pancreatic cancer, breast cancer, rectal cancer, colon cancer, medullary thyroid cancer and the like, EpCAM (epithelial cell adhesion molecule) overexpressed in liver cancer, stomach cancer, colorectal cancer, pancreatic cancer, breast cancer and the like, GD2 (disialoganglioside) overexpressed in neuroblastoma and the like, GPC3 (glypican 3) overexpressed in hepatocellular carcinoma and the like, PSMA (prostate-specific membrane antigen) overexpressed in prostate cancer and the like, TAG-72 (tumor-associated glycoprotein 72) overexpressed in ovarian cancer, breast cancer, colon cancer, lung cancer, pancreatic cancer and the like, GD3 (disialoganglioside) overexpressed in melanoma and the like, HLA-DR (human leukocyte antigen-DR) overexpressed in blood cancer, solid cancer and the like, MUC1 (Mucin 1) overexpressed in advanced solid cancer and the like, NY-ESO-1 (New York esophageal squamous cell carcinoma 1) overexpressed in advanced non-small-cell lung cancer and the like, LMP1 (latent membrane protein 1) overexpressed in nasopharyngeal neoplasms and the like, TRAILR2 (tumor-necrosis factor-related lysis-inducing ligand receptor) overexpressed in lung cancer, non-Hodgkin's lymphoma, ovarian cancer, colon cancer, colorectal cancer, pancreatic cancer and the like, VEGFR2 (vascular endothelial growth factor receptor 2), and HGFR (hepatocyte growth factor receptor) overexpressed in hepatocellular carcinoma and the like. Moreover, the surface antigen of cancer stem cells, such as CD44, CD166 or the like, may be a target molecule. Many target molecules overexpressed in cancer cells compared to normal cells are known in the art, and for other target molecules in addition to the examples listed above, reference may be made to the paper [Anne T Collins et al. Prospective Identification of Tumorigenic Prostate Cancer Stem Cells. Cancer Res. 2005 Dec. 1; 65(23):10946-51], the paper [Chenwei Li et al. Identification of Pancreatic Cancer Stem Cells. Cancer Res. 2007 Feb. 1; 67(3):1030-7], the paper [Shuo Ma et al. Current Progress in CAR-T Cell Therapy for Solid Tumors. Int. J. Biol. Sci. 2019 Sep. 7; 15(12):2548-2560], the paper [Dhaval S. Sanchala et al. Oncolytic Herpes Simplex Viral Therapy: A Stride Toward Selective Targeting of Cancer Cells. Front Pharmacol. 2017 May 16; 8:270] and the like.

In particular, the target molecule is preferably HER2 or CEA in the present invention.

The target cell targeted by the adapter of the recombinant HSV of the present invention is any cancer cell having a target molecule targeted by the cancer-cell-targeting domain of the adapter of the present invention. The cancer cell may be any type of carcinoma, such as esophageal cancer, stomach cancer, colorectal cancer, rectal cancer, oral cancer, pharyngeal cancer, laryngeal cancer, lung cancer, colon cancer, breast cancer, uterine cervical cancer, endometrial cancer, ovarian cancer, prostate cancer, testicular cancer, melanoma, bladder cancer, kidney cancer, liver cancer, pancreatic cancer, bone cancer, connective tissue cancer, skin cancer, brain cancer, thyroid cancer, leukemia, Hodgkin's disease, lymphoma, multiple myeloma, blood cancer, and the like.

In the present invention, the cell-targeting domain of the adapter may be an antibody derivative or an antibody analog in addition to a complete antibody having specific binding ability with the target molecule. The antibody derivative is a fragment of a complete antibody that includes at least one antibody variable region having specific binding ability with the target molecule, or is a modified antibody. Examples of the antibody derivative may include antibody fragments such as Fab, scFv, Fv, VhH, VH, VL, etc., multivalent or multispecific modified antibodies such as Fab2, Fab3, minibodies, diabodies, tribodies, tetrabodies, bis-scFv, etc., and the like. The antibody analog is an artificial peptide or polypeptide that has specific binding ability with the target molecule, like the antibody, but is different in structure from the antibody, and generally has a lower molecular weight than the antibody. Examples of the antibody analog may include ABD, Adhiron, affibody, affilins, affimers, alphabodies, anticalin, armadillo repeat protein, centyrins, DARPins, fynomers, a Kunitz region, pronectin, repebodies, and the like.

A considerably large number of papers in the art regarding the antibody, antibody derivative, antibody analog, and production thereof have accumulated, and examples thereof include the paper [Renate Kunert & David Reinhart, Advances in recombinant antibody manufacturing. Appl. Microbiol. Biotechnol. 2016 April; 100(8):3451-61], the paper [Holliger P, Hudson P. J., Engineered antibody fragments and the rise of single domains, Nat. Biotechnol. 2005 September; 23(9):1126-36], the paper [Xiaowen Yu et al., Beyond Antibodies as Binding Partners: The Role of Antibody Mimetics in Bioanalysis, Annual Review of Analytical Chemistry, 2017, 10:293-320], the paper [Abdul Rasheed Baloch et al., Antibody mimetics: promising complementary agents to animal-sourced antibodies, Critical Reviews in Biotechnology, 2016, 36:268-275], and the like.

In the present invention, the cell-targeting domain of the adapter is preferably an scFv (single-chain variable fragment). The scFv refers to a single-chain antibody in which the heavy-chain variable region (VH) and the light-chain variable region (VL) of an immunoglobulin are linked via a short linker peptide. In the scFv, the C-terminus of VH is linked to the N-terminus of VL, or the C-terminus of VL is linked to the N-terminus of VH. In the scFv, the linker peptide may be a linker peptide having any length and any sequence, so long as it does not interfere with the inherent three-dimensional structures of heavy and light chains and enables the heavy and light chains to be spatially adjacent to each other to thus have specific binding ability with the target molecule. Taking into consideration flexibility, solubility, resistance to proteolysis, etc., the linker is preferably composed of at least one selected from among amino acids such as Ser, Gly, Ala, Thr, etc., and the length thereof is 1-30 amino acids, preferably 3-25 amino acids, and more preferably 8-20 amino acids.

In the present invention, the target molecule targeted by scFv is HER2 or CEA. Specifically, scFv for HER2 is preferably configured such that VH of SEQ ID NO: 1 and VL of SEQ ID NO: 2 are linked in the order of VH, linker peptide and VL via a linker peptide (i.e. the C-terminus of VH is linked to the N-terminus of VL via the linker peptide), and scFv for CEA is preferably configured such that VL of SEQ ID NO: 3 and VH of SEQ ID NO: 4 are linked in the order of VL, linker peptide and VH via a linker peptide (i.e. the C-terminus of VL is linked to the N-terminus of VH via the linker peptide). Here, the linker peptide of scFv for HER2 preferably comprises the amino acid sequence of SEQ ID NO: 5, and the linker peptide of scFv for CEA preferably comprises the amino acid sequence of SEQ ID NO: 6.

In the present invention, the extracellular domain of HVEM may be HveA87 of SEQ ID NO: 9 (the HveA87 sequence comprising the leader sequence is represented in SEQ ID NO: 10), HveA102 of SEQ ID NO: 11 (the HveA102 sequence comprising the leader sequence is represented in SEQ ID NO: 12), or HveA107 of SEQ ID NO: 13 (the HveA107 sequence comprising the leader sequence is represented in SEQ ID NO: 14), which is disclosed in Korean Patent No. 10-0937774 and U.S. Pat. No. 8,318,662 (these documents are considered part of the present specification), in addition to HveA82 of SEQ ID NO: 7 (the HveA82 sequence comprising the leader sequence is represented in SEQ ID NO: 8), used in the following examples. HveA87, HveA102, and HveA107 comprise 5, 20, and 25 more amino acids than HveA82, respectively, and all of these may be used as HSV receptors of adapters, as confirmed in Korean Patent No. 10-0937774.

In the present invention, the linker sequence may be interposed between the cancer-cell-targeting domain and the extracellular domain of HVEM, and this linker sequence may be a linker having any length and any sequence, so long as it does not inhibit the function of each domain of the adapter. Preferably, the linker comprises at least one amino acid among the four amino acids Ser, Gly, Ala and Thr, and the length thereof may be 1-30 amino acids, preferably 3-25 amino acids, and more preferably 8-20 amino acids.

Also, the adapter of the present invention may be configured in the order of $NH_2$/cancer-cell-targeting domain/extracellular domain of HVEM/COOH or in the reverse order thereof. When the linker peptide is interposed therebetween, the adapter may be configured in the order of $NH_2$/cancer-cell-targeting domain/linker peptide/extracellular domain of HVEM/COOH or in the reverse order thereof.

The adapter of the present invention may be configured such that the leader sequence may be further attached to the N-terminus thereof, particularly the N-terminus of the cancer-cell-targeting domain (the N-terminus of VH or VL when scFv is used) in the adapter configuration in the order of $NH_2$/cancer-cell-targeting domain/linker peptide/extracellular domain of HVEM/COOH, or to the N-terminus of the extracellular domain of HVEM in the adapter configuration in the order of $NH_2$/extracellular domain of HVEM/linker peptide/cancer-cell-targeting domain/COOH. The leader sequence is a sequence that acts to induce the expression of the adapter in the target cells and the release of the adapter to the outside of the cells, and may also be omitted because the adapter acts to induce infection of the adjacent target cells with HSV only after the target cells are lysed and HSV is released.

In the present invention, in order to facilitate cloning, an amino acid corresponding to any restriction enzyme site may be interposed between VH and VL when scFv for the target molecule is used as the cell-targeting domain, between VH or VL and linker peptide when the linker peptide is disposed between VH and VL, between scFv and HVEM, between scFv and linker when the linker peptide is disposed between scFv and HVEM, or between linker and HVEM. For example, EF (base sequence: GAATTC) on which the restriction enzyme EcoRI acts or GS (base sequence: GGATCC) on which BamHI acts may be interposed, as shown in the following examples.

In the present invention, in order to express factors alone or in any combination for inducing or enhancing an immune response to cancer cells, the recombinant HSV may be configured such that a gene for the corresponding factor is inserted into the HSV genome. Such factors may be manipulated so as to express cytokines, chemokines, immune checkpoint antagonists (e.g. antibodies, antibody derivatives or antibody analogs, especially scFv), co-stimulatory factors capable of inducing activation of immune cells (T cells or NK cells), antagonists capable of inhibiting the function of TGFβ, which suppresses the immune response to cancer cells (e.g. antibodies, antibody derivatives or antibody analogs, especially scFv), heparanase capable of degrading heparan sulfate proteoglycan for a solid tumor microenvironment, antagonists capable of inhibiting the function of angiogenic receptor VEGFR-2 (VEGF receptor-2) (e.g. antibodies, antibody derivatives or antibody analogs, especially scFv), and the like.

As cytokines, for example, interleukins such as IL-2, IL-4, IL-7, IL-10, IL-12, IL-15, IL-18, IL-24, etc., interferons such as IFNα, IFNβ, IFNγ, etc., tumor necrosis factors such as TNFα, etc., and colony-stimulating factors such as GM-CSF, G-CSF, etc. may be used alone or in any combination of two or more thereof so as to be expressed in the recombinant HSV.

As chemokines, for example, CCL2 (C—C motif chemokine ligand 2), CCL5 (RANTES), CCL7, CCL9, CCL10, CCL12, CCL15, CCL19, CCL21, CCL20, and XCL-1 (X—C motif chemokine ligand 1) may be used alone or in combination so as to be expressed in the recombinant HSV.

As immune checkpoint antibodies, antagonists to PD-1 (programmed cell death 1), PD-L1 (programmed cell death ligand 1), PD-L2 (programmed cell death ligand 2), CD27 (cluster of differentiation 27), CD28 (cluster of differentiation 28), CD70 (cluster of differentiation 70), CD80 (cluster of differentiation 80), CD86 (cluster of differentiation 86), CD137 (cluster of differentiation 137), CD276 (cluster of differentiation 276), KIRs (killer-cell immunoglobulin-like receptors), LAG3 (lymphocyte activation gene 3), GITR (glucocorticoid-induced TNFR-related protein), GITRL (glucocorticoid-induced TNFR-related protein ligand), and CTLA-4 (cytolytic T lymphocyte associated antigen-4) may be used alone or in combination so as to be expressed in the recombinant HSV.

As co-stimulatory factors, CD2, CD7, LIGHT, NKG2C, CD27, CD28, 4-1BB, OX40, CD30, CD40, LFA-1 (lymphocyte function-associated antigen-1), ICOS (inducible T cell co-stimulator), CD3γ, CD3δ, and CD3ε may be used alone or in combination so as to be expressed in the recombinant HSV.

In the present invention, the recombinant HSV may be manipulated so as to express a prodrug-activating enzyme that converts a prodrug into a drug that is toxic to cancer cells. Examples of the prodrug-activating enzyme may include cytosine deaminase, which converts 5-FC (5-fluorocytosine) as a prodrug into 5-FU (5-fluorouracil) as a drug, rat cytochrome P450 (CYP2B1), which converts CPA (cyclophosphamide) as a prodrug into PM (phosphoramide mustard) as a drug, carboxylesterase, which converts irinotecan (SN-38150) as a prodrug into SN-38 as a drug, bacterial nitroreductase, which converts BC1954 as a prodrug into 4-hydroxylamine151 as a DNA cross-linker, PNP (purine nucleoside phosphorylase) isolated from *E. coli*, which converts 6-methylpurine-2'-deoxyriboside as a prodrug into 6-methylpurine as a drug, and the like.

Moreover, in the present invention, the recombinant HSV may be manipulated so as to express TRAIL (TNF-related lysis-inducing ligand). TRAIL is known to induce lysis of cancer cells by binding to the receptor thereof, which is overexpressed in cancer cells (Kaoru Tamura et al. Multimechanistic Tumor Targeted Oncolytic Virus Overcomes Resistance in Brain Tumors. Mol. Ther. 2013 January; 21(1):68-77).

For more details regarding the use of factors or prodrug-activating enzymes to induce or enhance these immune responses, reference may be made to the paper [Michele Ardolino et al., Cytokine treatment in cancer immunotherapy, J. Oncotarget, Oncotarget. 2015 Aug. 14; 6(23):], the paper [Bernhard Homey et al. Chemokines: Agents for the Immunotherapy of Cancer. Nat Rev Immunol. 2002 March; 2(3):175-84], the paper [Marianela Candolfi et al., Evaluation of proapoptotic transgenes to use in combination with Flt3L in an immune-stimulatory gene therapy approach for Glioblastoma multiforme (GBM), J. FASEB J., 2008, 22:107713], the paper [Danny N Khalil et al. The Future of Cancer Treatment: Immunomodulation, CARs and Combination Immunotherapy. Nat Rev Clin Oncol. 2016 May; 13(5):273-90], the paper [Paul E Hughes et al. Targeted Therapy and Checkpoint Immunotherapy Combinations for the Treatment of Cancer. Trends Immunol. 2016 July; 37(7): 462-476], the paper [Cole Peters, Samuel D. Rabkin, Designing herpes viruses as oncolytics, Mol. Ther Oncolytics. 2015; 2:15010], and the like.

In the present invention, as in the aforementioned adapter, the factors or prodrug-activating enzymes to induce or enhance immune responses are configured such that the expression cassette of the gene thereof (i.e. a construct in which the gene thereof is operably linked with a promoter sequence that enables expression thereof and a polyadenylation signal sequence) is inserted into the HSV genome without inhibiting the proliferation of HSV. Such insertion may be performed without deletion of the HSV genome, or insertion into loci from which some or all of non-essential genes in the HSV genome are deleted may be conducted. Here, upon insertion without deletion of the HSV genome, insertion may be performed between genes, and preferred insertion loci are, for example, between UL3 and UL4 genes, between UL26 and UL27 genes, between UL37 and UL38 genes, between UL48 and UL49 genes, between UL53 and UL54 genes, and between US1 and US2 genes. Upon insertion into loci from which non-essential genes are deleted or into genes without deletion of non-essential genes, such non-essential genes may be selected from among any non-essential genes as described above.

Another aspect of the present invention pertains to a pharmaceutical composition for anti-cancer treatment containing the recombinant HSV described above as an active ingredient.

The pharmaceutical composition of the present invention has anti-cancer effects against a carcinoma expressing a target molecule targeted by the targeting domain of the adapter expressed by the recombinant HSV. Examples of the carcinoma are as described above in relation to the target molecule.

In particular, it is preferable that the composition of the present invention have anti-cancer effects against carcinoma having tumor cells expressing CEA or HER2. Examples of tumor cells expressing CEA include colorectal cancer cells, stomach cancer cells, lung cancer cells, breast cancer cells, rectal cancer cells, colon cancer cells, and liver cancer cells, and examples of tumor cells expressing HER2 include breast cancer cells, ovarian cancer cells, stomach cancer cells, lung cancer cells, head and neck cancer cells, osteosarcoma cells, glioblastoma multiforme cells, and salivary gland tumor cells.

In the present invention, anti-cancer effects include lysis of cancer cells, decreased viability of cancer cells, inhibition or delay of pathological symptoms of cancer due to suppression of cancer cell proliferation, inhibition or delay of onset of such pathological symptoms, inhibition of cancer metastasis, and inhibition of cancer recurrence.

The pharmaceutical composition of the present invention may further include a recombinant adapter molecule in addition to the recombinant HSV as the active ingredient. The recombinant adapter molecule means that a fused protein having a cancer-cell-targeting domain, as in the adapter expressed by the recombinant HSV, or more precisely, as in the fused protein of the cancer-cell-targeting domain and the extracellular domain of HVEM, is produced through a recombination process. Here, having the cancer-cell-targeting domain as in the adapter expressed by the recombinant HSV means that when the target molecule targeted by the cancer-cell-targeting domain of the adapter expressed by HSV is HER2, the target molecule targeted by the cancer-cell-targeting domain of the adapter molecule is also HER2. The method of producing the target protein of interest using a recombination process typically includes preparing an expression vector able to express a target protein and transforming the expression vector into host cells such as *E. coli*, yeast or animal cells (CHO cells, NSO cells, BHK cells, Sp2 cells, or HEK-293 cells), followed by culture and then isolation of the target protein, and the method of producing the target protein of interest using a recombination process is well known in the art (Sambrook et al., Molecular Cloning, A Laboratory Manual, Cold Spring Harbor Laboratory Press, (2001)). In particular, with regard to the production of the recombinant adapter molecule used in the present invention, reference may be made to Korean Patent No. 10-0937774 and U.S. Pat. No. 8,318,662. The pharmaceutical composition of the present invention further includes such a recombinant adapter molecule, and thus, when the recombinant HSV, which is the active ingredient of the present invention, and the recombinant adapter molecule are administered together to a patient, the initial infection efficiency of the recombinant HSV is effectively increased.

Moreover, the pharmaceutical composition of the present invention may be used in combination with or in a mixture with an approved anti-cancer agent. Examples of the anti-cancer agent may include any anti-cancer agents, any cytokine drugs, any antibody drugs, any immune checkpoint inhibitor drugs, and any cell therapeutic agents (for car-T cell therapy or car-NK cell therapy), which exhibit cytotoxicity to cancer cells, such as metabolic antagonists, alkylating agents, topoisomerase antagonists, microtubule antagonists, and plant-derived alkaloids. Specific examples thereof may include taxol, nitrogen mustard, imatinib, oxaliplatin, gefitinib, bortezomib, sunitinib, carboplatin, cisplatin, rituximab, erlotinib, sorafenib, IL-2 drug, IFN-α drug, IFN-γ drug, trastuzumab, blinatumomab, ipilimumab, pembrolizumab, nivolumab, atezolizumab, durvalumab, bevacizumab, cetuximab, tisagenlecleucel (Kymriah), axicabtagene ciloleucel (Yescarta), and the like. In addition to the exemplified anti-cancer agents, other anti-cancer agents known in the art may be used without limitation in combination with or in a mixture with the pharmaceutical composition of the present invention.

The pharmaceutical composition of the present invention may include a pharmaceutically acceptable carrier or excipient, and may thus be prepared in the form of an oral formulation or a parenteral formulation through a typical method known in the art depending on the route of administration.

Such a pharmaceutically acceptable carrier or excipient does not impair the activity or properties of the drug and is not itself toxic to the human body, and examples thereof may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water (e.g. saline and sterile water), syrup, methyl cellulose, methylhydroxybenzoate, propylhydroxybenzoate, talc, magnesium stearate, mineral oil, Ringer's solution, buffer, maltodextrin solution, glycerol, ethanol, dextran, albumin, and any combination thereof. In particular, when the pharmaceutical composition of the present invention is formulated in the form of a liquid solution, an appropriate carrier or excipient may include saline, sterile water, Ringer's solution, buffered saline, albumin injection solution, dextrose solution, maltodextrin solution, glycerol, and ethanol, which may be used alone or in combination. If necessary, other typical pharmaceutical additives, such as antioxidants, buffers and bacteriostatic agents, may be added and used.

When the pharmaceutical composition of the present invention is prepared into an oral formulation, it may be manufactured in the form of a tablet, troche, capsule, elixir, suspension, syrup, wafer, etc., and when prepared into a parenteral formulation, especially an injection, it may be manufactured in a unit dose ampoule or a multi-dose form. The pharmaceutical composition of the present invention may also be manufactured in the form of a solution, suspension, tablet, pill, capsule, sustained-release preparation, and the like.

The pharmaceutical composition of the present invention may be formulated in a unit dosage form suitable for administration to a patient's body according to a typical method in the pharmaceutical field, and may be administered through an oral route of administration or a parenteral route of administration, such as dermal, intralesional, intravenous, intramuscular, intraarterial, intramedullary, intrathecal, intraventricular, pulmonary, transdermal, subcutaneous, intraperitoneal, intranasal, intradigestive-tract, topical, sublingual, intravaginal, and rectal routes, using any administration method commonly used in the art.

The dose (effective amount) of the pharmaceutical composition of the present invention may vary depending on factors such as the formulation method, the administration mode, the patient's age, weight and gender, pathological conditions, diet, administration time, administration route, excretion rate and response sensitivity, and may be appropriately determined by those skilled in the art in consideration of these factors. In a preferred embodiment, the pharmaceutical composition of the present invention is prepared as an injection in a unit dosage form. When prepared as an injection in a unit dosage form, the amount of the recombinant HSV included per unit dose of the pharmaceutical composition of the present invention may range from $10^2$-$10^{14}$ pfu, particularly $10^4$-$10^{11}$ pfu.

Still another aspect of the present invention pertains to a method of treating or preventing cancer (tumors), including administering a pharmaceutical composition containing the recombinant HSV as described above to a subject such as a patient in an effective amount.

The method of treating cancer is made possible by lysing and killing cancer cells having a target molecule targeted by the cancer-cell-targeting domain of the adapter of the recombinant HSV. Therefore, the treatment method of the present invention may be applied to any carcinoma having such a target molecule. In particular, the treatment method of the present invention is preferably applied to a carcinoma expressing CEA or HER2.

The treatment method of the present invention may be used without limitation in combination with the other cancer treatment methods as described above. For example, the cytotoxic anti-cancer agents, cytokine drugs, antibody drugs, immune checkpoint inhibitor drugs, cell therapeutic agents (for car-T cell therapy or car-NK cell therapy), radiotherapy, surgery, etc., as exemplified above, may be used before or after administration of the composition of the present invention or in a manner of simultaneous administration in combination with the composition of the present invention.

In the treatment method of the present invention, the effective amount is an amount in which the pharmaceutical composition of the present invention is administered so as to exhibit the intended medical effect, such as a cancer treatment or prevention effect, when the pharmaceutical composition of the present invention is administered to a subject such as a patient for the administration period based on the recommendation of a medical expert, etc. As described above, such an effective amount may be appropriately determined by a person skilled in the art, such as a medical expert, etc., depending on the patient's age, weight and gender, pathological conditions, and the like, as described above.

In the treatment method of the present invention, the pharmaceutical composition is preferably administered in the form of an injection to a patient or the like in a mode of parenteral administration, for example, intralesional (intratumoral), intravenous, intramuscular, intra-arterial administration, etc.

As described above, according to the present invention, a recombinant HSV containing an expression cassette capable of expressing a fused protein of a cell-targeting domain and an extracellular domain of HVEM and the use thereof can be provided.

When the recombinant HSV infects and enters target cells, which are cancer cells, HSV proliferates, and an adapter, which is the fused protein, is expressed in the cells and is released to the outside of the cells along with the proliferated HSV virion upon cell lysis, or is continuously released even before the virion is released due to cell lysis when the adapter contains a leader sequence. The fused protein released to the outside of the cells acts to induce the HSV virion to infect surrounding cancer cells expressing a target molecule recognized by the cancer-cell-targeting domain or to increase the infection efficiency thereof.

DETAILED DESCRIPTION

A better understanding of the present invention will be given through the following examples. However, these examples are not to be construed as limiting the scope of the present invention.

<Example 1> Production of HVEM-Restricted HSV-1

Figure 1:
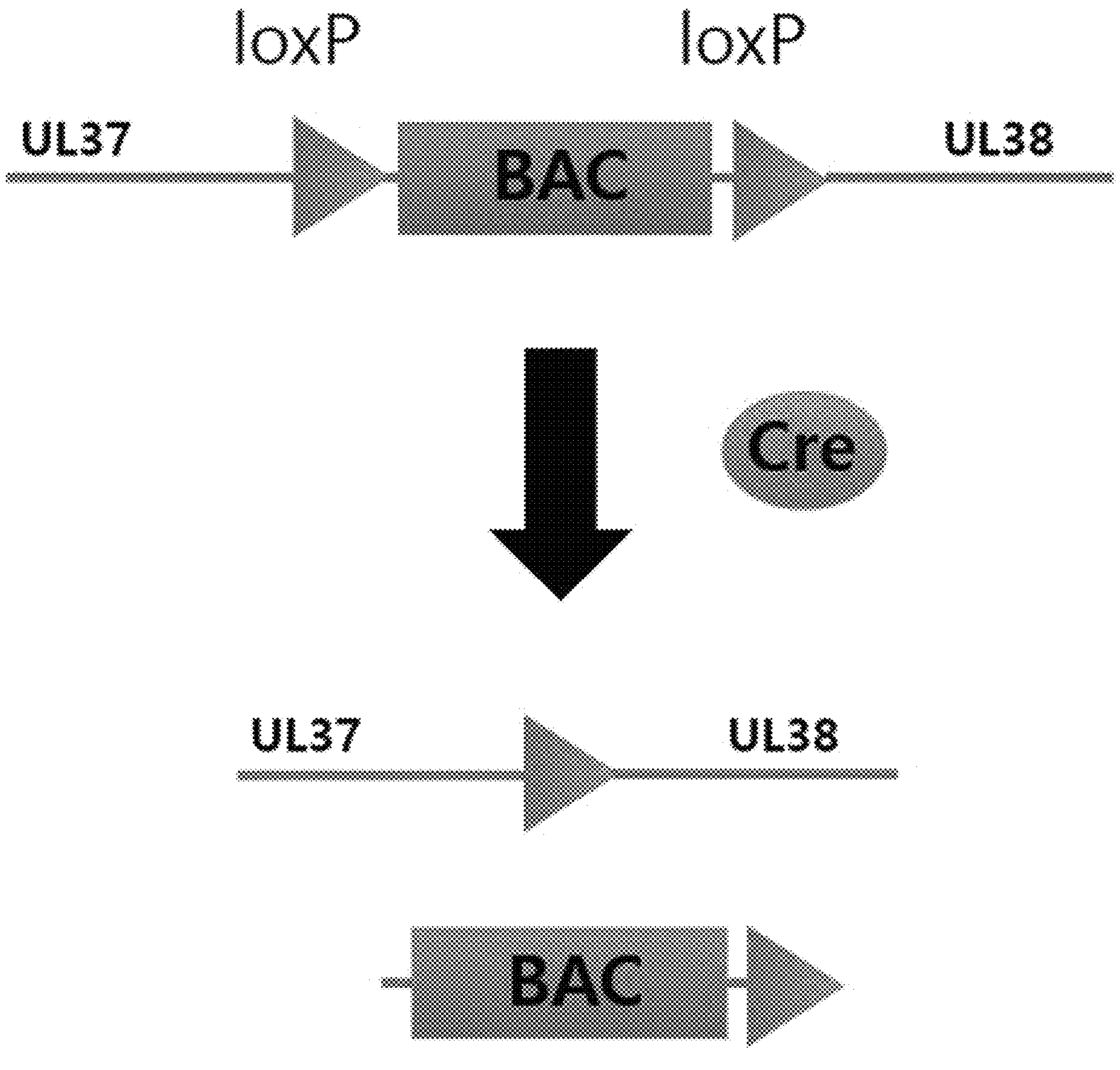
FIG. 1 schematically shows the genomic structure of KOS-37 BAC and the excision of BAC by a Cre-Lox system.

An HSV-1 gene is composed of a large gene of about 152 kb, and thus KOS-37 BAC (GenBank Accession No. MF156583) (Gierasch W. W. et al. J. Virol. Methods. 2006. 135:197-206) was used to insert a foreign gene or introduce a mutation into a specific locus. An HSV-1 KOS strain is a kind of HSV-1 strain mainly used in laboratories because of the well-known characteristics thereof and the usefulness thereof for investigation of gene function and etiology (Smith K O. Proc. Soc. Exp. Biol. Med. 1964. 115:814-816). KOS-37 BAC, manufactured by inserting a BAC plasmid into a KOS gene, enables cloning at the bacterial level through transformation of DH10B bacteria (Invitrogen) (Gierasch W. W. et al.; J. Virol. Methods. 2006. 135:197-206). In the KOS-37 BAC, a bacterial artificial chromosome (BAC) is inserted along with a LoxP site at both sides thereof into a locus between UL37 and UL38 of the HSV-1 KOS genome. This is designed to remove the BAC gene using a Cre-Lox system in subsequent procedures. The schematic view thereof is shown in FIG. 1.

In order to manufacture HVEM-restricted HSV-1, which enters cells only through the HVEM cell receptor, a gD-R222N/F223I HSV-1 virus, in which arginine (R) at position 222 and phenylalanine (F) at position 223 of the HSV-1 gD amino acid sequence (GenBank Accession No. ASM47818, SEQ ID NO: 15) are substituted with asparagine (N) and isoleucine (I), respectively, was manufactured.

The gD-R222N/F223I HSV-1 virus manufactured through mutation is able to infect host cells only through HVEM (HveA) rather than nectin-1 as the cell entry receptor (Uchida H et al., J. Virol. 2009. 83(7):2951-2961).

Figure 2:
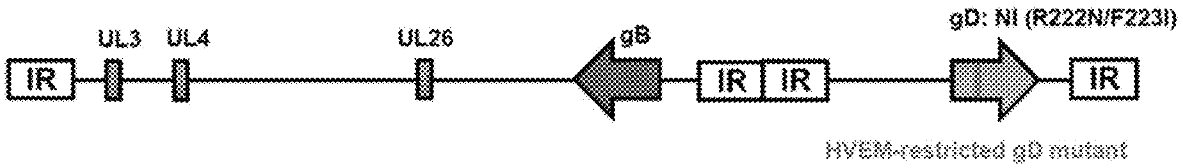
FIG. 2 schematically shows the genomic structure of a KOS-gD-R222N/F223I virus, which is HVEM-restricted HSV-1.

The genomic structure of HVEM-restricted HSV-1 is schematically shown in FIG. 2.

The gD-R222N/F223I HSV-1 virus was manufactured by introducing R222N/F223I mutations into the gD site of KOS-37 BAC according to the manufacturer's protocol using a counter selection BAC modification kit (GeneBridges, Inc.).

Specifically, an *E. coli* clone containing KOS-37 BAC was transformed with a pRed/ET plasmid expressing RecE and RecT capable of performing the function of homologous recombination (Muyrers J. P. et al.; Nucleic Acids Res. 1999. 27(6):1555-1557). A gD-rpsL-neo/kan cassette was manufactured using a set of homologous region primers (forward primer gD-rpsL For: SEQ ID NO: 16, reverse primer gD-rpsL Rev: SEQ ID NO: 17) including a locus to introduce a mutation into gD. The gD-rpsL-neo/kan cassette is composed of the rpsL gene, which is a selective marker that confers sensitivity to streptomycin, and the gD homologous region at the insertion locus, and the neo/kan gene that confers kanamycin resistance. When the gD-rpsL-neo/kan cassette is inserted, *E. coli* having sensitivity to streptomycin antibiotics by the rpsL gene and kanamycin resistance by the neo/kan gene is manufactured. After inducing the expression of RecE and RecT so as to enable homologous recombination by activating the function of pRed/ET by adding L-arabinose (Sigma-Aldrich) to the *E. coli* clone containing KOS-37 BAC and pRedET (Muyrers J P et al.; Nucleic Acids Res. 1999. 27(6):1555-1557), transformation with 200 ng of the manufactured gD-rpsL-neo/kan cassette was performed. Through homologous recombination, the gD-rpsL-neo/kan cassette is inserted into the gD locus of KOS-37 BAC. *E. coli* in which gD-rpsL-neo/kan is inserted into KOS-37 BAC has kanamycin resistance, but streptomycin resistance is blocked by the rpsL gene. It was inferred for *E. coli* selected from the kanamycin medium that gD-rpsL-neo/kan was inserted therein, and the final step of inserting a gene was performed. After inducing the expression of RecE and RecT so as to enable homologous recombination by activating the function of pRed/ET by adding L-arabinose (Sigma-Aldrich) to *E. coli* containing the KOS 37-BAC gD-rpsL-neo/kan clone, transformation with 100 pmol of R222N_F223I_mutant, which is an oligonucleotide encoding gD (SEQ ID NO: 18) substituted with N and I at positions 222 and 223 of gD, was performed. Based on the principle whereby streptomycin resistance blocked by rpsL is activated while replacing the existing gD-rpsL-neo/kan cassette with the inserted oligonucleotide, candidates were selected in a streptomycin medium (Heermann R. et al., Microb. Cell Fact. 2008. 14: doi: 10.1186). In the selected candidates, DNA was isolated using a DNA preparation method (Horsburgh B C et al., Methods Enzymol. 1999. 306:337-352), and the substitution of N and I at respective positions 222 and 223 of gD was confirmed through PCR (polymerase chain reaction) and DNA sequencing.

Next, for viral production, the completed KOS-BAC-gD-R222N/F223I DNA was extracted using a large-construct DNA purification kit (Macherey-Nagel), after which $2\times10^5$ Cre-Vero-HVEM cells were transfected with 1 μg of DNA using a Lipofectamine 2000 reagent (Invitrogen). Then, cell culture was carried out using DMEM (Dulbecco's Modified Eagle's Medium) (Welgene) containing 100 U/ml penicillin/100 μg/ml streptomycin (Welgene) and 10% FBS (fetal bovine serum, Welgene). The Cre-Vero-HVEM cell line is a cell line inducing HVEM protein expression by inserting the HVEM gene into the Cre-Vero cell line (Gierasch et al.; J. Virol. Methods. 2006. 135:197-206). The reason for using Cre-Vero-HVEM is that the BAC gene of KOS 37 BAC may be removed using Cre recombinase of the cells and also that infection with the KOS-gD-R222N/F223I virus due to HVEM overexpression is effective, and thus mass production of viruses becomes easy. 3-4 days after DNA transfection, the formation of a plaque was confirmed, after which the virus-containing cells were collected, subjected three times to a freeze-thaw process (Gierasch W. W. et al.; J. Virol. Methods. 2006. 135:197-206) and sonicated, ultimately obtaining a KOS-gD-R222N/F223I virus.

<Example 2> Production of HVEM-Restricted HSV-1 Expressing EmGFP

An expression cassette capable of expressing EmGFP (Emerald Green Fluorescent Protein) was inserted into the gene UL26/UL27 locus of the KOS-gD-R222N/F223I virus manufactured in Example 1 above. This is to facilitate the observation of viral production and infection using EmGFP as a marker. A pCDNA6.2-GW/EmGFP-miR plasmid (Invitrogen) was used to manufacture the EmGFP cassette.

Figure 3:
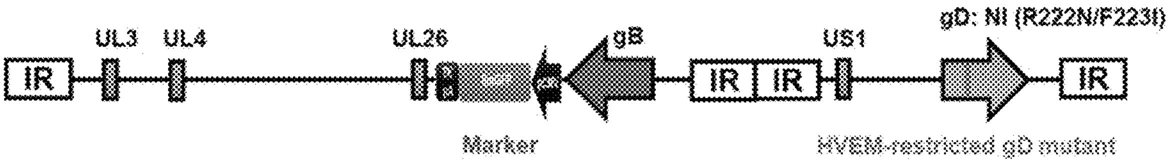
FIG. 3 schematically shows the genomic structure of a KOS-EmGFP-gD-R222N/F223I virus, which is HVEM-restricted HSV-1 expressing EmGFP.

The genomic structure of HVEM-restricted HSV-1 expressing UL26/27-EmGFP is schematically shown in FIG. 3.

For EmGFP expression, pCMV-EmGFP-tkpA using a gene promoter of cytomegalovirus and tkpA as a polyadenylation signal of HSV TK (herpes simplex virus thymidine kinase) was inserted into KOS-BAC-gD-R222N/F223I.

All insertion methods were carried out according to the manufacturer's protocol using a counter selection BAC modification kit (GenBridges. Inc) as in Example 1 above.

Specifically, an *E. coli* clone containing the KOS-BAC-gD-R222N/F223I genome was transformed with a pRed/ET plasmid expressing RecE and RecT capable of performing the function of homologous recombination (Muyrers J P et al.; Nucleic Acids Res. 1999. 27(6):1555-1557). A UL26/27-rpsL-neo/kan cassette was manufactured using a set of homologous region primers (forward primer UL26/27-rpsL_For: SEQ ID NO: 19, reverse primer UL26/27-rpsL_Rev: SEQ ID NO: 20) including a locus to introduce a target gene between UL26 and UL27. The clone containing KOS-BAC-gD-R222N/F223I and pRed/ET was added with L-arabinose (Sigma-Aldrich) to thus induce homologous recombination, followed by transformation with 200 ng of the manufactured UL26/27-rpsL-neo/kan cassette. The UL26/27-rpsL-neo/kan cassette was inserted into the UL26/27 locus of KOS-BAC-gD-R222N/F223I through homologous recombination. *E. coli* into which UL26/27-rpsL-neo/kan was inserted has kanamycin resistance, but streptomycin resistance is blocked by the rpsL gene. It was inferred for *E. coli* selected from the kanamycin medium that UL26/27-rpsL-neo/kan was inserted therein, and the final step of inserting a gene was performed.

*E. coli* containing the UL26/27-rpsL-neo/kan cassette was added with L-arabinose (Sigma-Aldrich) activating the function of pRed/ET to thus induce homologous recombination, followed by transformation with 200 ng of the UL26/27-tkpA-EmGFP-pCMV cassette. The UL26/27-tkpA-EmGFP-pCMV cassette was manufactured using a pCDNA6.2-GW/EmGFP-miR plasmid (Invitrogen) as a template, a forward primer UL26-tkpA_For (SEQ ID NO: 21) and a reverse primer UL27-pCMV_Rev (SEQ ID NO: 22).

Based on the principle whereby streptomycin resistance blocked by rpsL is activated while replacing the existing UL26/27-rpsL-neo/kan cassette with the inserted UL26/27-tkpA-EmGFP-pCMV, candidates were selected in a streptomycin medium (Heermann R et al., Microb. Cell Fact. 2008. 14: doi: 10.1186). DNA was isolated from the selected candidates using a DNA preparation method (Horsburgh B C et al., Methods Enzymol. 1999. 306:337-352). The introduction of tkpA-EmGFP-pCMV in UL26/27 was confirmed through EcoRI and XhoI treatment and PCR (polymerase chain reaction), and the exact gene sequence was identified through sequencing of the PCR product.

An experiment was conducted for normal expression of a fluorescent protein and production of a virus. The completed KOS-BAC-EmGFP-gD-R222N/F223I DNA was extracted using a large-construct DNA purification kit (Macherey-Nagel), after which $2\times10^5$ Cre-Vero-HVEM cells were transfected with 1 μg of DNA using a Lipofectamine 2000 reagent (Invitrogen). 3 days after transfection, the fluorescence expression of EmGFP was observed using a fluorescence microscope, and viral production was observed through the plaque formation of Cre-Vero-HVEM cells. After confirmation of the plaque formation, the virus-containing cells were collected, subjected three times to a freeze-thaw process (Gierasch W W et al.; J. Virol Methods. 2006. 135:197-206) and sonicated, thus obtaining a KOS-EmGFP-gD-R222N/F223I virus.

For infection with the KOS-EmGFP-gD-R222N/F223I virus and fluorescence expression thereof, HVEM free cell lines (J1 and J-Nectin) and cell lines expressing HVEM (J-HVEM) were used. J1 cells are young hamster kidney cell lines that are deficient in HVEM and nectin-1 as virus HSV-1 receptors (Petrovic B. et al., 2017. PLoS Pathog. 19; 13(4):e1006352). The J-Nectin and J-HVEM cell lines are cell lines that overexpress nectin-1 and HVEM respectively in J1 cells (Petrovic B. et al., 2017. PLoS Pathog. 19; 13(4):e1006352). Each cell line was cultured in DMEM (Welgene) containing 100 U/ml penicillin/100 μg/ml streptomycin (Welgene) and 10% FBS (fetal bovine serum, Welgene). $1\times10^4$ cells were infected at 10 MOI (multiplicity of infection) with the KOS-EmGFP-gD-R222N/F223I virus obtained above, and after 24 hr, the fluorescent protein expression and viral infection were observed using a fluorescence microscope (Baek H. J. et al., Mol. Ther. 2011. 19(3):507-514).

Figure 4:
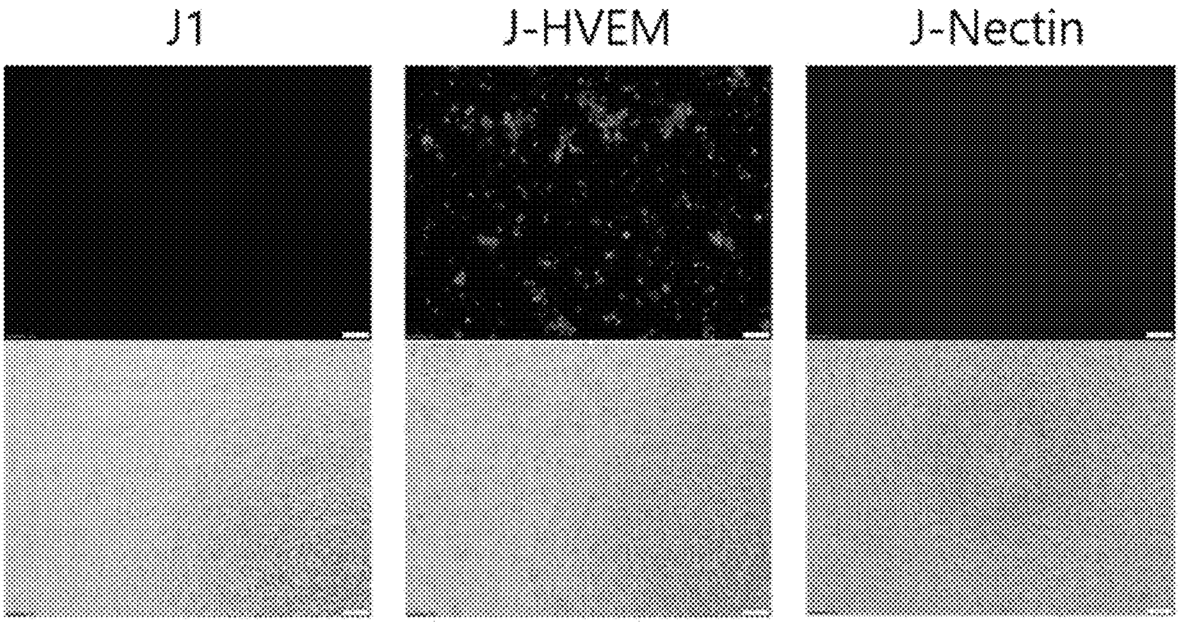
FIG. 4 shows the results of fluorescence expression of HVEM-restricted HSV-1 expressing EmGFP and specific infection of cells having an HVEM receptor therewith.

The results thereof are shown in FIG. 4, upper and lower images of which were taken using a fluorescence microscope and an optical microscope, respectively. With reference to the upper fluorescence microscope images of FIG. 4, it can be seen that the J1 cell line and the J-Nectin cell line were not infected, and only the J-HVEM cell line was infected.

Based on the above results, it was confirmed that the infection with the KOS-EmGFP-gD-R222N/F223I virus was easily observed through the expression of the fluorescent protein, as intended, and cell entry became possible using only HVEM as the cell entry receptor, rather than nectin-1.

<Example 3> Production of KOS-EmGFP-Gd-R222N/F223I Virus Expressing HER2scFv-HveA Adapter, HveA-HER2scFv Adapter, and CEAscFv-HveA Adapter Each of a HER2scFv-HveA adapter-expressing cassette, an HveA-HER2scFv adapter-expressing cassette, and a CEAscFv-HveA adapter-expressing cassette were inserted into the gene UL3/UL4 locus of the KOS-EmGFP-gD-R222N/F223I virus having the EmGFP expression cassette (tkpA-EmGFP-pCMV) inserted therein, manufactured in Example 2.

Figure 5:
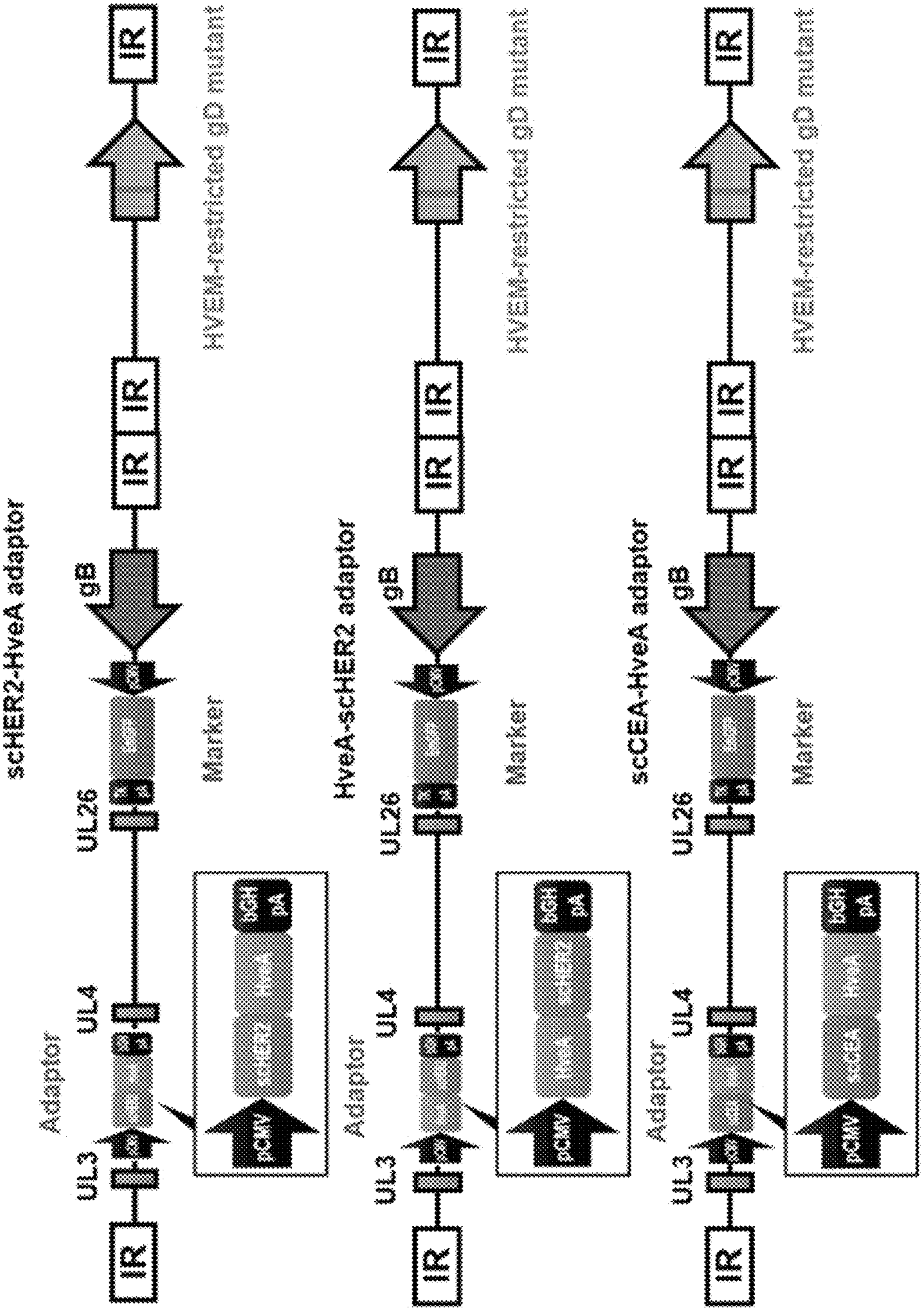
FIG. 5 schematically shows the genomic structure of a HER2scFv-HveA adapter-expressing KOS-HER2scFv-HveA-EmGFP-gD/R222N/F223I virus, the genomic structure of an HveA-HER2scFv adapter-expressing KOS-HveA-HER2scFv-EmGFP-gD/R222N/F223I virus, and the genomic structure of a CEAscFv-HveA adapter-expressing KOS-CEAscFv-HveA-EmGFP-gD/R222N/F223I virus.
Figure 6:
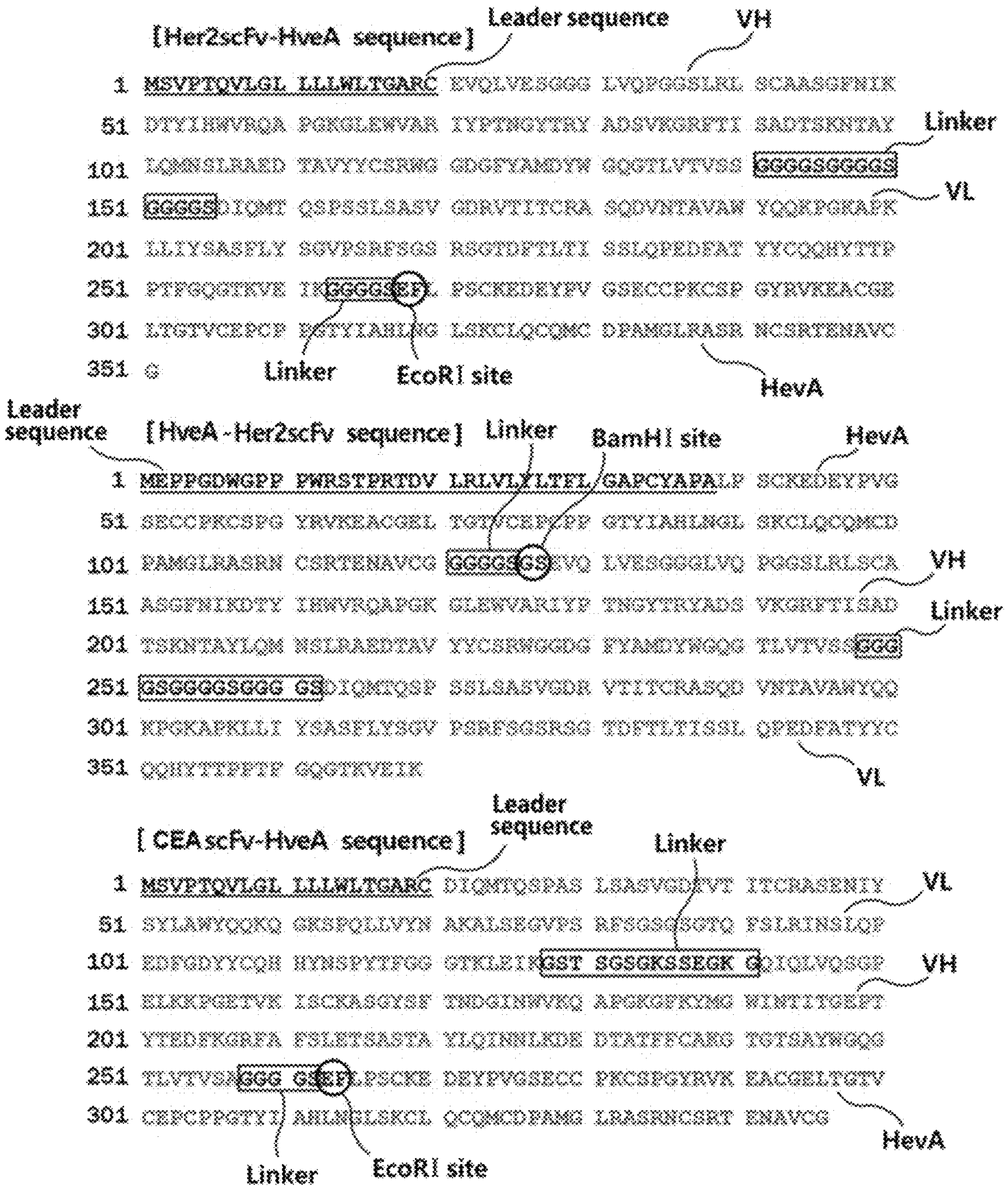
FIG. 6 shows the entire sequence of the HER2scFv-HveA adapter SEQ ID NO: 23), HveA-HER2scFv adapter (SEQ ID NO: 25) and CEAscFv-HveA adapter (SEQ ID NO: 2) and the corresponding sequence.

The KOS-HER2scFv-HveA-EmGFP-gD/R222N/F223I virus genome into which pCMV-HER2scFv-HveA-bGHpA as the HER2scFv-HveA adapter-expressing cassette was inserted, the KOS-HveA-HER2scFv-EmGFP-gD/R222N/F223I virus genome into which pCMV-HveA-HER2scFv-bGHpA as the HveA-HER2scFv adapter-expressing cassette was inserted, and the KOS-CEAscFv-HveA-EmGFP-gD/R222N/F223I virus genome into which pCMV-CEAscFv-HveA-bGHpA as the CEAscFv-HveA adapter-expressing cassette was inserted are schematically shown in FIG. 5. Moreover, FIG. 6 shows the entire sequence of the HER2scFv-HveA adapter, the HveA-HER2scFv adapter, and the CEAscFv-HveA adapter, and the corresponding sequence. Here, scFv for HER2 is configured such that VH of SEQ ID NO: 1 and VL of SEQ ID NO: 2 are linked via a linker peptide of SEQ ID NO: 5, scFv for CEA is configured such that VL of SEQ ID NO: 3 and VH of SEQ ID NO: 4 are linked via a linker peptide of SEQ ID NO: 6, and HveA is HveA82 of SEQ ID NO: 7 excluding the leader sequence in the HER2scFv-HveA adapter and the CEAscFv-HveA adapter, and is Hve82 of SEQ ID NO: 8 including the leader sequence in the HveA-HER2scFv adapter. Also, in the HER2scFv-HveA adapter and the CEAscFv-HveA adapter, the leader sequence of SEQ ID NO: 33 is included in the N-terminus, namely in front of VH of HER2scFv and VL of CEAscFv.

After the scFv sequence for HER2 or CEA and the $NH_2$-GGGGS sequence, which is the linker sequence of the HveA sequence, EF (base sequence: GAATTC), which is a restriction enzyme EcoRI site for easy cloning, is added, and after the HveA sequence and the $NH_2$-GGGGS sequence, which is the linker sequence of the scFv sequence for Her2, GS (base sequence: GGATCC), which is a restriction enzyme BamHI site for easy cloning, is added, and is also a sequence that may be excluded from the adapter. bGHpA is a bGH-PolyA (bovine growth hormone polyadenylation) signal sequence. The amino acid sequence and gene sequence of the full length of the HER2scFv-HveA adapter used in this example are represented in SEQ ID NO: 23 and SEQ ID NO: 24, respectively, the amino acid sequence and gene sequence of the full length of the HveA-HER2scFv adapter are represented in SEQ ID NO: 25 and SEQ ID NO: 26, respectively, and the amino acid sequence and gene sequence of the full length of the CEAscFv-HveA adapter are represented in SEQ ID NO: 27 and SEQ ID NO: 28, respectively.

The insertion of the HER2scFv-HveA adapter-expressing cassette, the HveA-HER2scFv adapter-expressing cassette, and the CEAscFv-HveA adapter-expressing cassette was performed according to the manufacturer's protocol using a counter selection BAC modification kit (GeneBridges. Inc) as in Examples 1 and 2.

Specifically, the *E. coli* clone containing the KOS-BAC-EmGFP-gD-R222N/F223I genome manufactured in Example 2 was transformed with a pRed/ET plasmid expressing RecE and RecT capable of performing the function of homologous recombination (Muyrers J P et al.; Nucleic Acids Res. 1999. 27(6):1555-1557). A UL3/4-rpsL-neo/kan cassette was manufactured using a set of homologous region primers (forward primer HSV-1_UL3/4-rpsL-neo_for: SEQ ID NO: 29, reverse primer HSV-1_UL3/4-rpsL-neo_rev: SEQ ID NO: 30) including a locus to introduce a target gene between UL3 and UL4. The clone containing KOS-BAC-EmGFP-gD-R222N/F223I and pRedET was added with L-arabinose (Sigma-Aldrich) to thus induce homologous recombination, followed by transformation with 200 ng of the UL3/4-rpsL-neo/kan cassette manufactured above. Through such homologous recombination, the UL3/4-rpsL-neo/kan cassette was inserted into the UL3/4 locus of KOS-BAC-EmGFP-gD-R222N/F223I. *E. coli* into which UL3/4-rpsL-neo/kan was inserted has kanamycin resistance, but streptomycin resistance is blocked by the rpsL gene. It was inferred for *E. coli* selected from the kanamycin medium that UL3/4-rpsL-neo/kan was inserted therein, and the final step of inserting a target gene was performed.

*E. coli* containing the UL3/4-rpsL-neo/kan cassette was added with L-arabinose (Sigma-Aldrich) activating the function of pRed/ET to thus induce homologous recombination, followed by transformation with 200 ng of each of the UL3/4-pCMV-Her2scFv-HveA-bGHpA cassette, the UL3/4-pCMV-HveA-Her2scFv-bGHpA cassette and the UL3/4-pCMV-CEAscFv-HveA-bGHpA cassette. The UL3/4-pCMV-Her2scFv-HveA-bGHpA cassette, the UL3/4-pCMV-HveA-Her2scFv-bGHpA cassette and the UL3/4-pCMV-CEAscFv-HveA-bGHpA cassette were manufactured using a forward primer HSV-1_UL3/4-HM_pCMV_For (SEQ ID NO: 31) and a reverse primer UL3/4_bGH_poly_R (SEQ ID NO: 32) using, as a template, a pCDNA3.1-HER2scFv-HveA plasmid, a pCDNA3.1-HveA-HER2scFv plasmid, and a pCDNA3.1-CEAscFv-HveA plasmid (Baek H. J. et al., Mol. Ther. 2011. 19(3): 507-514).

Based on the principle whereby streptomycin resistance blocked by rpsL is activated while replacing the conventionally inserted UL3/4-rpsL-neo/kan cassette with the above inserted UL3/4-pCMV-Her2scFv-HveA-bGHpA, UL3/4-pCMV-HveA-Her2scFv-bGHpA and UL3/4-pCMV-CEAscFv-HveA-bGHpA, candidates were selected in a streptomycin medium (Heermann R et al., Microb Cell Fact. 2008. 14: doi: 10.1186). DNA was isolated from the selected candidates using a DNA preparation method (Horsburgh B C et al., Methods Enzymol. 1999. 306:337-352). The introduction of the UL3/4-pCMV-Her2scFv-HveA-bGHpA, UL3/4-pCMV-HveA-Her2scFv-bGHpA and UL3/4-pCMV-CEAscFv-HveA-bGHpA into UL3/4 was confirmed through restriction enzyme EcoRI and XhoI treatment and PCR (polymerase chain reaction), and the exact gene sequence was identified through sequencing of the PCR product.

The completed KOS-BAC-Her2scFv-HveA-EmGFP-gD-R222N/F223I, KOS-BAC-HveA-Her2scFv-EmGFP-gD-R222N/F223 and KOS-BAC-CEAscFv-HveA-EmGFP-gD/R222N/F223I DNA were extracted using a large-construct DNA purification kit (Macherey-Nagel), after which $2\times10^5$ Cre-Vero-HVEM cells were transfected with 1 μg of DNA using a Lipofectamine 2000 reagent (Invitrogen). 3 days after transfection, the fluorescence expression of EmGFP and the plaque formation of cells were observed using a fluorescence microscope. After confirmation of the plaque formation, the virus-containing cells were collected, subjected three times to a freeze-thaw process (Gierasch W W et al.; J. Virol Methods. 2006. 135:197-206) and sonicated, thus obtaining a KOS-Her2scFv-HveA-EmGFP-gD-R222N/F223I virus, a KOS-HveA-Her2scFv-EmGFP-gD-R222N/F223I virus, and a KOS-CEAscFv-HveA-EmGFP-gD/R222N/F223I virus.

<Example 4> Targeting of HER2- or CEA-Expressing Cancer Cells Using Adapter-Expressing Oncolytic Virus

<Example 4-1> Targeting of HER2-Expressing Cancer Cells Using HER2scFv-HveA Adapter-Expressing Oncolytic Virus In order to evaluate whether viral infection of surrounding cancer cells or lysis after infection is induced by expressing the HER2scFv-HveA adapter using the HER2scFv-HveA adapter-expressing KOS-Her2scFv-HveA-EmGFP-gD-R222N/F223I virus manufactured in Example 3, the following experiment was carried out.

The cell lines that were used in the experiment were cell lines (J1, CHO-K1, MDA-MB-231) not expressing HER2 and cell lines (J-HER2, CHO-HER2, SK-OV-3) expressing HER2. The Chinese hamster ovary cell lines CHO-K1 and CHO-HER2 (Kuroki M et al., J. Biol. Chem. 1991. 74:10132-10141) were cultured using a HaM's F-12K medium (Welgene) containing 100 U/ml penicillin/100 μg/ml streptomycin (Welgene) and 10% FBS (fetal bovine serum), and J1 and J-HER2 (Petrovic B et al., 2017. PLoS Pathog. 19; 13(4):e1006352), a breast cancer cell line MDA-MB-231 (ATCC, HTB-26), and an ovarian cancer cell line SK-OV-3 (ATCC, HTB-77) were cultured using DMEM containing 100 U/ml penicillin/100 μg/ml streptomycin (Welgene) and 10% FBS.

For HER2-specific viral infection, $1\times10^4$ J cell lines at 10 MOI, $1.5\times10^4$ CHO cell lines at 1 MOI, and $1\times10^4$ SK-OV-3 and MDA-MB-231 cell lines at 0.1 MOI were infected with the HER2scFv-HveA adapter-expressing virus manufactured in Example 3. After 90 min, the medium was replaced with a fresh medium to remove the remaining early virus and the HER2scFv-HveA adapter. 3 days after infection, viral infection of each cell line was observed through fluorescence expression using a fluorescence microscope (Baek H. J. et al., Mol. Ther. 2011. 19(3):507-514).

Figure 7:
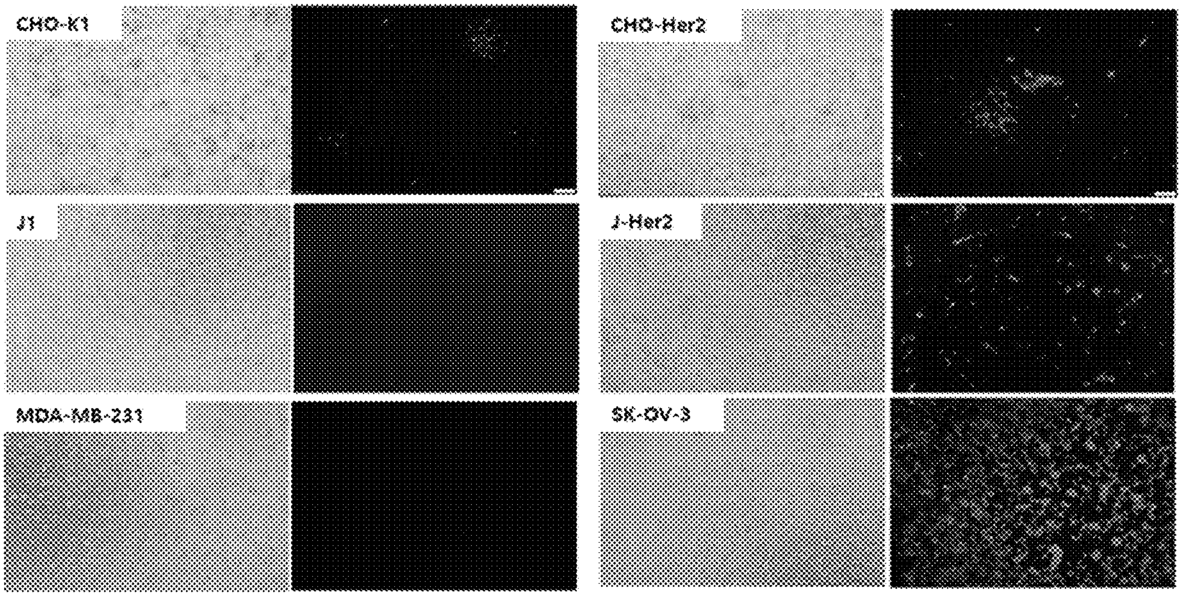
FIG. 7 shows the results of specific infection of HER2-expressing cells with the HER2scFv-HveA adapter-expressing KOS-HER2scFv-HveA-EmGFP-gD/R222N/F223I virus.

The results thereof are shown in FIG. 7, left and right images of which were taken using an optical microscope and a fluorescence microscope, respectively. With reference to the right fluorescence microscope images of FIG. 7, it can be confirmed that CHO-Her2, J-Her2, and SK-OV-3, which are cell lines expressing HER2, were specifically infected. The HSV-1 infection pathway has a mechanism of action of attachment of gB and gC to cells and cell entry by gD. The reason why the HER2scFv-HveA-expressing gD R222N/F223I mutated virus causes slight infection of the CHO-K1 cell line, lacking in HVEM and nectin-1, is that slight infection also occurs through cell attachment of gB and gC, in addition to the function of gD (Baek H. J. et al., Mol. Ther. 2011. 19(3):507-514).

Also, CHO-Her2, J-Her2, and SK-OV-3, which are cell lines expressing HER2, were first infected with the virus despite the lack of the HVEM receptor. The reason for this is that the HER2scFv-HveA adapter-expressing virus manufactured in Example 3 used for infection contains a trace amount of the HER2scFv-HveA adapter bound to gD of the virus or the expressed HER2scFv-HveA adapter during viral production through Cre-Vero-HVEM cells.

Figure 8:
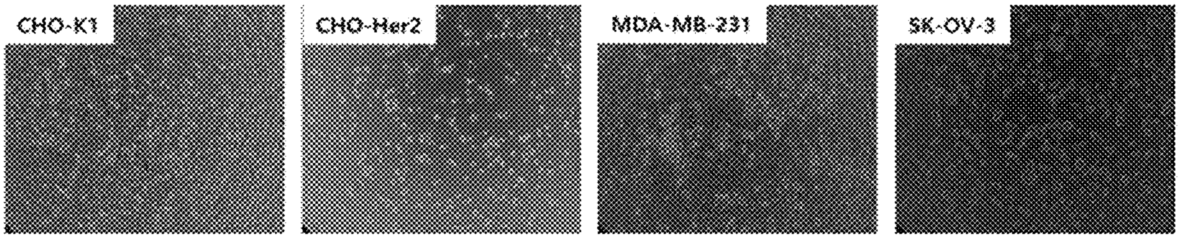
FIG. 8 shows the results of specific lysis of HER2-expressing cells with the HER2scFv-HveA adapter-expressing KOS-HER2scFv-HveA-EmGFP-gD/R222N/F223I virus.

In order to observe lysis caused by the virus, $1.5\times10^4$ CHO-K1 and CHO-Her2 cell lines were infected at 1 MOI with the HER2scFv-HveA adapter-expressing virus, and $1\times10^4$ SK-OV-3 and MDA-MB-231 cell lines were infected at 2 MOI with the HER2scFv-HveA adapter-expressing virus. 3 days after infection, each cell line was observed using an optical microscope. The results thereof are shown in FIG. 8. In the case of CHO-Her2 and SK-OV-3, which are cell lines expressing HER2, it can be seen that the number of cells was much lower than that of CHO-K1 and MDA-MB-231, which are cell lines not expressing HER2.

Figure 9:
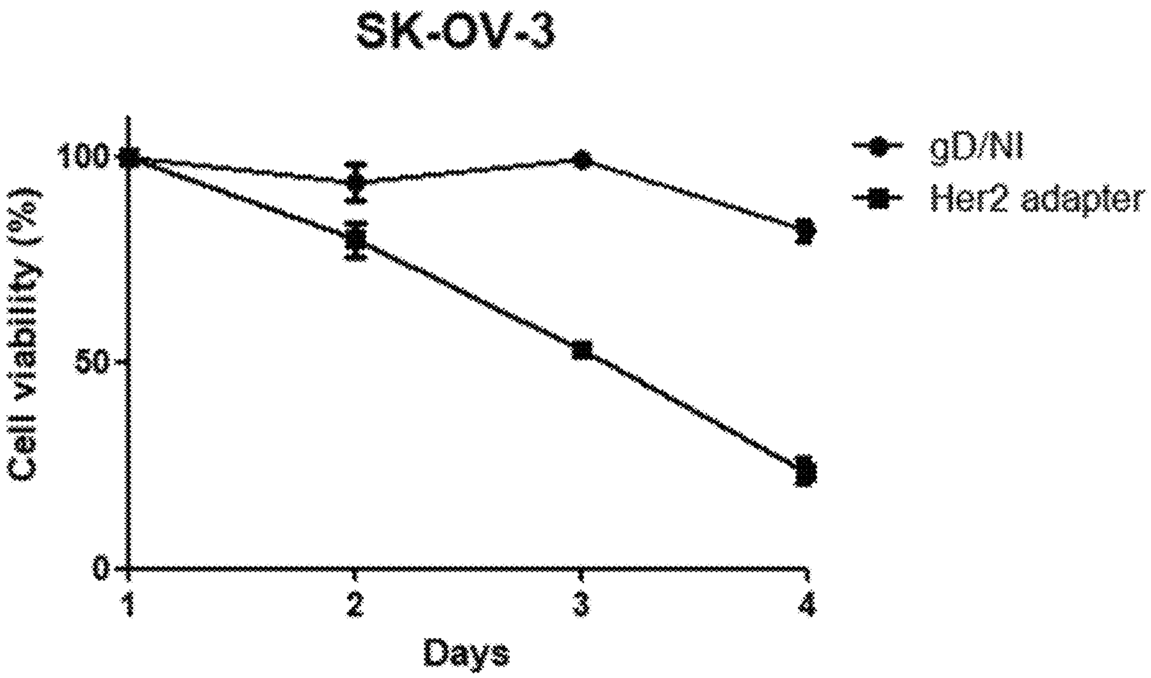
FIG. 9 shows the results of comparison of lysis of HER2-expressing cells with a wild-type virus (HSV-1 KOS) and a HER2scFv-HveA adapter-expressing KOS-HER2scFv-HveA-EmGFP-gD/R222N/F223I virus (Her2 adapter)

Also, $1\times10^4$ SK-OV-3 cells, which are the cell line expressing HER2, were infected at 2 MOI with each of an HVEM-restricted herpes virus (gD/NI) and a HER2scFv-HveA adapter-expressing virus (Her2 Adapter), and lysis was observed on the $1^{st}$, $2^{nd}$, $3^{rd}$, $4^{th}$ and $5^{th}$ day through cell staining using Alamar blue (Sigma). The results thereof are shown in FIG. 9. It can be seen that the effect of the HER2scFv-HveA adapter-expressing virus (Her2 Adapter) on inducing lysis was much higher than that of a general herpes virus (HSV-1 KOS).

<Example 4-2> Targeting of CEA-Expressing Cancer Cells Using CEAscFv-HveA Adapter-Expressing Oncolytic Virus In order to evaluate whether viral infection of surrounding cancer cells is induced by expressing CEAscFv-HveA using the CEAscFv-HveA adapter-expressing KOS-CEAscFv-HveA-EmGFP-gD/R222N/F223I virus manufactured in Example 3, the following experiment was carried out.

The cell lines that were used in the experiment were cell lines (CHO-K1) not expressing CEA and cell lines (CHO-CEA, MKN45) expressing CEA. The Chinese hamster ovary cell lines CHO-K1 and CHO-CEA cell lines (Kuroki M et al., J. Biol. Chem. 1991. 74:10132-10141) were cultured using a HaM's F-12K medium (Welgene) containing 100 U/ml penicillin/100 μg/ml streptomycin (Welgene) and 10% FBS, and a stomach cancer cell line MKN45 (JCRB, JCRB0254) was cultured using an RPMI-1640 medium containing 100 U/ml penicillin/100 μg/ml streptomycin (Welgene) and 10% FBS (Baek H. J. et al., Mol. Ther. 2011. 19(3):507-514).

For CEA-specific viral infection, $1.5\times10^4$ CHO-K1 and CHO-CEA cells were infected at 10 MOI with the virus. After 90 min, the medium was replaced with a fresh medium to remove the remaining early virus and the CEAscFv-HveA adapter. After 72 hr, the extent of viral infection of each cell line was observed using a fluorescence microscope.

Figure 10:
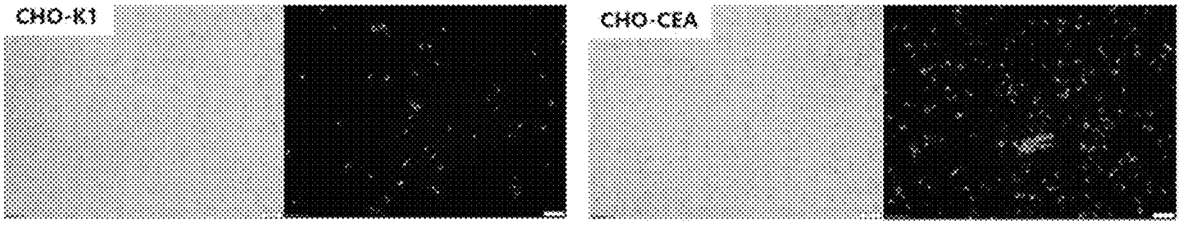
FIG. 10 shows the results of specific infection of CEA-expressing cells with a CEAscFv-HveA adapter-expressing KOS-CEAscFv-HveA-EmGFP-gD/R222N/F223I virus.

The results thereof are shown in FIG. 10, left and right images of which were taken using an optical microscope and a fluorescence microscope, respectively. With reference to the right fluorescence microscope images of FIG. 10, CHO-K1 cell lines were rarely infected, and CHO-CEA cell lines were observed to be infected.

The reason why the CEAscFv-HveA-expressing gD R222N/F223I mutated virus causes slight infection of the CHO-K1 cell line, lacking in HVEM and nectin-1, is that, as described above, slight infection also occurs through cell attachment of gB and gC, in addition to the function of gD (Baek H. J. et al., Mol. Ther. 2011. 19(3):507-514).

Also, in order to confirm specific infection of CEA-expressing cancer cells, $6\times10^4$ MKN45 cell lines were infected at 1 MOI with each of the KOS-EmGFP-gD-R222N/F223I virus (gD/NI, control) manufactured in Example 2 and the KOS-CEAscFv-HveA-EmGFP-gD-R222N/F223I (scCEA-HveA) obtained in Example 3. After 90 min, the medium was replaced with a fresh medium to remove the remaining early virus and the CEAscFv-HveA adapter. After 72 hr, the extent of viral infection of each cell line was observed using a fluorescence microscope.

Figure 11:
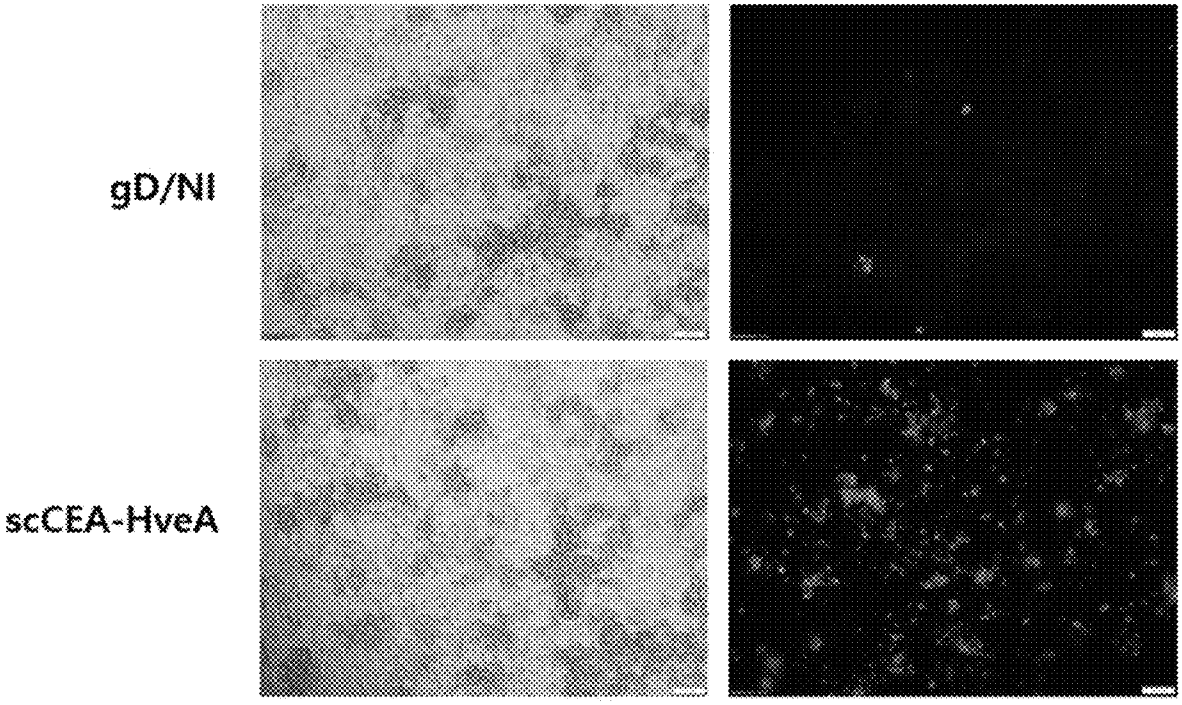
FIG. 11 shows the results of comparison of specific infection of CEA-expressing cells with a KOS-EmGFP-gD-R222N/F223I virus (gD/NI), which is HVEM-restricted HSV-1 expressing EmGFP, and with a CEAscFv-HveA adapter-expressing KOS-CEAscFv-HveA-EmGFP-gD/R222N/F223I virus.

The results thereof are shown in FIG. 11, left and right images of which were taken using an optical microscope and a fluorescence microscope, respectively. With reference to the images on the right, it can be seen that the MKN45 cancer cells were specifically infected with the KOS-CEAscFv-HA-EmGFP-gD-R222N/F223I virus, rather than the KOS-EmGFP-gD-R222N/F223I virus as the control.

<Example 5> Change in Infection Activity of Adapter-Expressing Oncolytic Virus Depending on Structural Change of HER2 Adapter In order to evaluate changes in the infection activity depending on the adapter structure by expressing the HER2scFv-HveA adapter or the HveA-HER2scFv adapter using the HER2scFv-HveA adapter-expressing KOS-Her2scFv-HveA-EmGFP-gD-R222N/F223I virus and the HveA-HER2scFv adapter-expressing KOS-HveA-HER2scFv-EmGFP-gD-R222N/F223I virus, having different adapter structures manufactured in Example 3, the following experiment was carried out.

The cell lines that were used in the experiment were CHO-K1 cell lines not expressing HER2 and CHO-HER2 cell lines expressing HER2. The Chinese hamster ovary cell lines CHO-K1 and CHO-HER2 (Kuroki M et al., J. Biol. Chem. 1991. 74:10132-10141) were cultured using a HaM's F-12K medium (Welgene) containing 100 U/ml penicillin/100 μg/ml streptomycin (Welgene) and 10% FBS (fetal bovine serum).

In order to evaluate changes in the activity of viral infection depending on the adapter structure, $1.5\times10^4$ CHO- K1 and CHO-HER2 cell lines were infected at 1 MOI with each of the HER2scFv-HveA adapter-expressing virus and the HveA-HER2scFv adapter-expressing virus manufactured in Example 3. After 90 min, the medium was replaced with a fresh medium to remove the remaining early virus and the HER2scFv-HveA and HveA-HER2scFv adapters. 3 days after infection, the cells were stained with VP16, which is a protein essential for transcription of the early gene of the virus, and the infection with the adapter-expressing viruses having different adapter structures was observed using a fluorescence microscope (Baek H. J. et al., Mol. Ther. 2011. 19(3):507-514).

Figure 12:
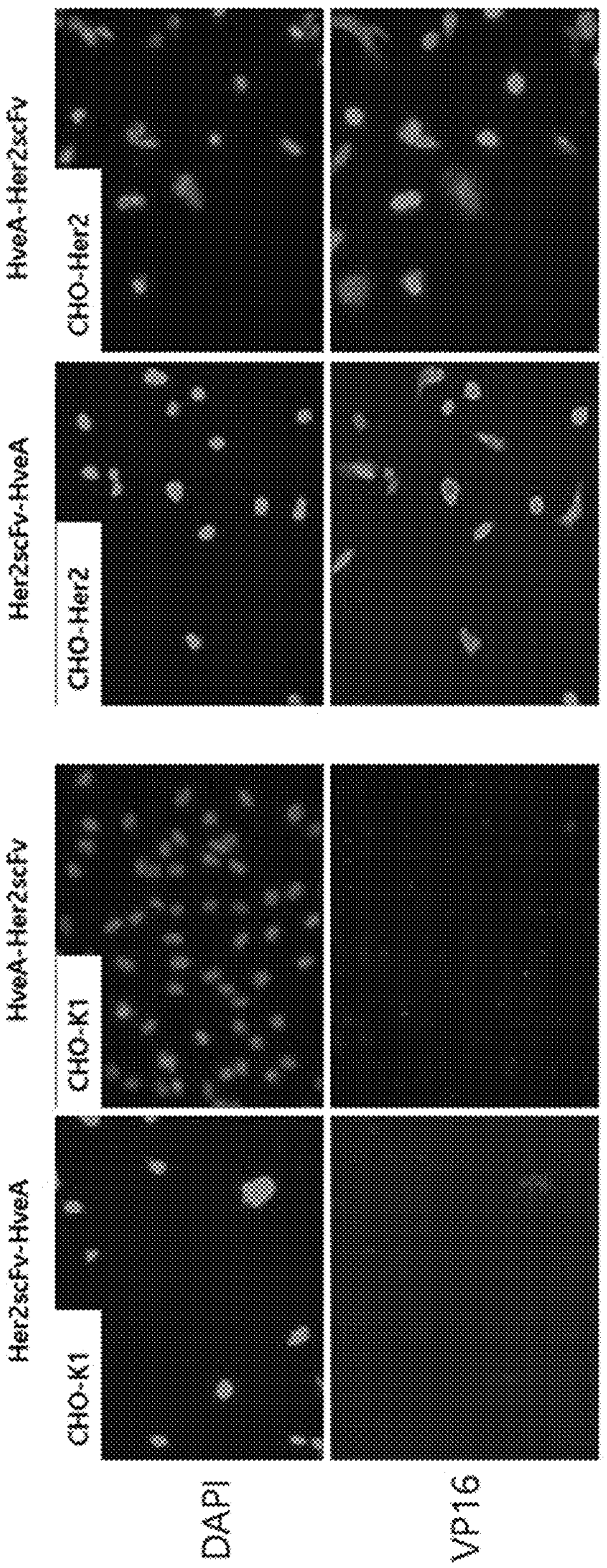
FIG. 12 shows the results of comparison of specific infection with a HER2scFv-HveA adapter-expressing KOS-HER2scFv-HveA-EmGFP-gD/R222N/F223I virus and an HveA-HER2scFv adapter-expressing KOS-HveA-HER2scFv-EmGFP-gD/R222N/F223I virus.

With reference to the images on the right of FIG. 12, showing the extent of infection of CHO-HER2 cells with the adapter-expressing viruses having different adapter structures through VP16 staining, the infection levels with the HER2scFv-HveA and HveA-HER2scFv adapter-expressing viruses were similar. In the adapter-expressing system, it was confirmed that there was no difference in the extent of infection due to the position of HveA, and it was confirmed for both structures that HER2-specific infection activity was high. DAPI (4',6-diamidino-2-phenylindole) was used as a comparative observation indicator for VP16 staining through nucleic acid staining.

The reason why the HER2scFv-HveA or HveA-HER2scFv-expressing gD R222N/F223I mutated virus causes slight infection of the CHO-K1 cell line, lacking in HVEM and nectin-1, is that, as described above, slight infection also occurs through cell attachment of gB and gC, in addition to the function of gD (Baek H. J. et al., Mol. Ther. 2011. 19(3):507-514).

Also, CHO-Her2, which is the HER2-expressing cell line, was first infected with the virus despite the lack of the HVEM receptor. The reason for this is that the HER2scFv-HveA or HveA-HER2scFv adapter-expressing virus manufactured in Example 3 used for infection contains a trace amount of the HER2scFv-HveA adapter or HveA-HER2scFv adapter bound to gD of the virus or the expressed HER2scFv-HveA during viral production through Cre-Vero-HVEM cells.

<Example 6> Extracellular Expression of Adapter of Adapter-Expressing Virus and Observation of Viral Spreading to Surrounding Cancer Cells In order to confirm the release of the HER2scFv-HveA adapter expressed in the cells by the HER2scFv-HveA adapter-expressing KOS-Her2scFv-HveA-EmGFP-gD-R222N/F223I virus manufactured in Example 3 to the outside of the cells, the following experiment was carried out.

The cell line that was used in the experiment was a Vero-HVEM cell line (Gierasch et al.; J. Virol. Methods. 2006. 135:197-206). The Vero-HVEM cell line was cultured using DMEM (Dulbecco's Modified Eagle's Medium (Welgene)) containing 100 U/ml penicillin/100 μg/ml streptomycin (Welgene) and 10% FBS (fetal bovine serum, Welgene). $2.0\times10^5$ Vero-HVEM cells were infected at 0.1 MOI with KOS-Her2scFv-HveA-EmGFP-gD-R222N/F223I and, as a control, a KOS-EmGFP-gD-R222N/F223I virus. After 90 min, the medium was replaced with a fresh medium not containing FBS to remove the remaining early virus and the HER2scFv-HveA adapter. After 48 hr, the medium was collected. The extent of protein expression was measured through Western blotting in order to confirm the HER2scFv-HveA adapter expression of the collected medium.

Figure 13:
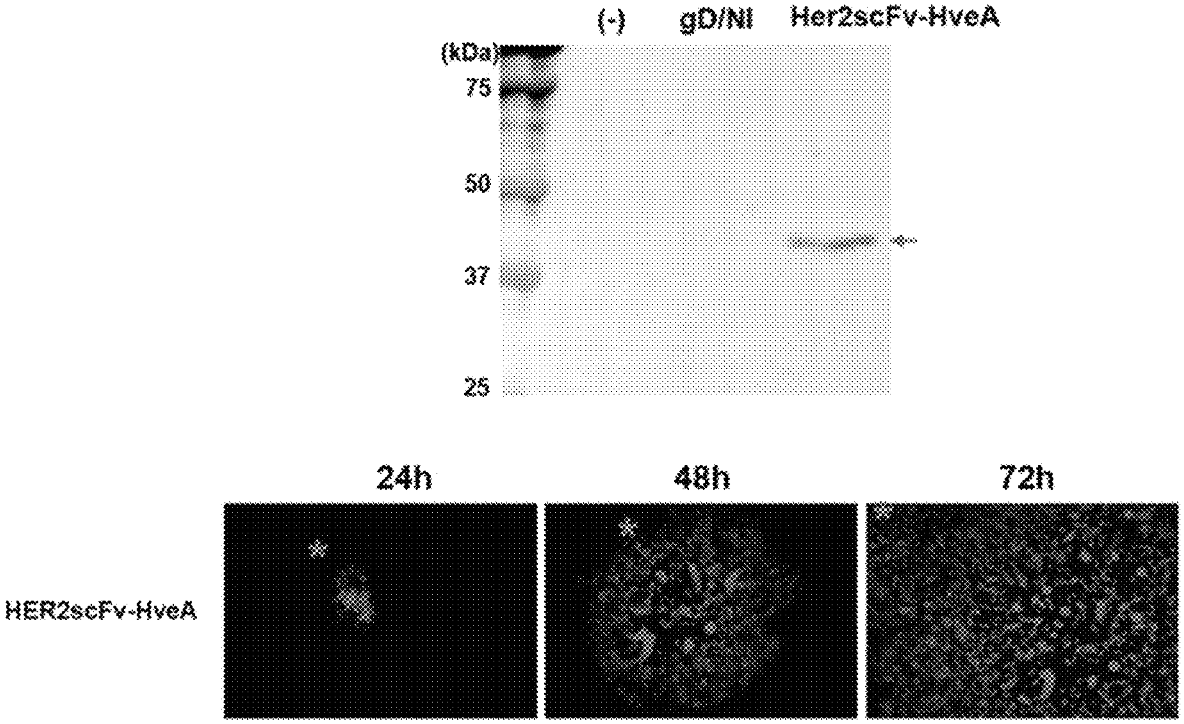
FIG. 13 shows the results of extracellular expression of an adapter of a HER2scFv-HveA adapter-expressing virus and of observation of spreading of viral infection to surrounding cancer cells.

The results thereof are shown at the top of FIG. 13. As shown in the results at the top of FIG. 13, the expression of the adapter was not detected in the medium obtained from the group infected with the KOS-EmGFP-gD-R222N/F223I virus (gD/NI) not containing the adapter, but the adapter released to the outside of the cells was detected in the medium obtained from the group infected with the KOS-Her2scFv-HveA-EmGFP-gD-R222N/F223I virus (Her2scFv-HveA).

Based on the above results, it was confirmed that the expression of the inserted adapter and the release thereof to the outside of the cells proceeded efficiently through intracellular infection of the KOS-Her2scFv-HveA-EmGFP-gD-R222N/F223I virus, as intended.

Moreover, in order to observe spreading of viral infection to surrounding cancer cells due to cell lysis and additionally due to the adapter released to the outside of the cells, the following experiment was carried out.

The cell line that was used in the experiment was a SK-OV-3 cell line. As an ovarian cancer cell line, the SK-OV-3 cell line was cultured using DMEM (Dulbecco's Modified Eagle's Medium (Welgene)) containing 100 U/ml penicillin/100 μg/ml streptomycin (Welgene) and 10% FBS (fetal bovine serum, Welgene).

And then, $1\times10^4$ SK-OV-3 cell lines were diluted and infected at 0.01 MOI with a KOS-Her2scFv-HveA-EmGFP-gD-R222N/F223I virus. The reason for viral dilution and infection is to observe spreading of viral infection to surrounding cancer cells. The viral infection and spreading was observed using a fluorescence microscope.

The results thereof are shown at the bottom of FIG. 13. As shown in the results at the bottom of FIG. 13, 24 hr after infection, one group infected with the KOS-Her2scFv-HveA-EmGFP-gD-R222N/F223I virus was observed. Then, after 48 hr and 72 hr had passed, the viral infection was observed to have rapidly spread to the surrounding cancer cells in the first infected group.

Based on the above results, as intended, through intracellular infection of the KOS-Her2scFv-HveA-EmGFP-gD-R222N/F223I virus, the inserted adapter was released to the outside of the cells and was bound to the antigen on the surface of the surrounding cancer cells, and the pattern whereby the virus released due to cell lysis targeted the adapter bound to the cancer cells or spread infection to the surrounding cancer cells expressing a target molecule using the adapter bound to the virus was confirmed.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A recombinant herpes simplex virus (HSV), in which an adapter expression cassette expressing a fusion protein of a cancer-cell-targeting domain and an extracellular domain of HVEM is inserted into a genome of the herpes simplex virus without inhibiting proliferation of the herpes simplex virus, wherein the adapter expression cassette expressing the fusion protein is inserted between UL3 and UL4 genes, between UL26 and UL27 genes, between UL37 and UL38 genes, between UL48 and UL49 genes, between UL53 and UL54 genes or between US1 and US2 genes in the genome of the virus, and wherein the gene encoding glycoprotein D (gD) is mutated so as to prevent the encoded gD from binding to nectin-1 while still retaining the ability of said gD to bind to HVEM.

2. The recombinant herpes simplex virus of claim 1, wherein the extracellular domain of HVEM is HveA82, comprising an amino acid sequence of SEQ ID NO: 7 or 8, HveA87, comprising an amino acid sequence of SEQ ID NO: 9 or 10, HveA102, comprising an amino acid sequence of SEQ ID NO: 11 or 12, or HveA107, comprising an amino acid sequence of SEQ ID NO: 13 or 14.

3. The recombinant herpes simplex virus of claim 1, wherein the fusion protein is configured such that the cancer-cell-targeting domain and the extracellular domain of HVEM are linked via a linker peptide comprising 1 to 30 amino acids.

4. The recombinant herpes simplex virus of claim 3, wherein the linker peptide comprises at least one amino acid selected from among Ser, Gly, Ala and Thr.

5. The recombinant herpes simplex virus of claim 1, wherein the cancer-cell-targeting domain is a domain that recognizes and binds to a target molecule of a cancer cell that is a target cell, and the target molecule is an antigen or a receptor on a surface of the cancer cell, which is expressed only in the cancer cell or is overexpressed in the cancer cell compared to a normal cell.

6. The recombinant herpes simplex virus of claim 5, wherein the antigen or the receptor is EGFRvIII, EGFR, a metastin receptor, a receptor tyrosine kinase, HER2 (human epidermal growth factor receptor 2), a tyrosine kinase-18-receptor (c-Kit), HGF receptor c-Met, CXCR4, CCR7, an endothelin-A receptor, PPAR-δ (peroxisome proliferator activated receptor δ), PDGFR-α (platelet-derived growth factor receptor α), CD133, CEA (carcinoembryonic antigen), EpCAM (epithelial cell adhesion molecule), GD2 (disialoganglioside), GPC3 (Glypican 3), PSMA (prostate-specific membrane antigen), TAG-72 (tumor-associated glycoprotein 72), GD3 (disialoganglioside), HLA-DR (human leukocyte antigen-DR), MUC1 (Mucin 1), NY-ESO-1 (New York esophageal squamous cell carcinoma 1), LMP1 (latent membrane protein 1), TRAILR2 (tumor-necrosis factor-related lysis-inducing ligand receptor), VEGFR2 (vascular endothelial growth factor receptor 2), HGFR (hepatocyte growth factor receptor), CD44 or CD166.

7. The recombinant herpes simplex virus of claim 1, wherein the cancer-cell-targeting domain is a domain that recognizes and binds to HER2, which is a target molecule of a cancer cell that is a target cell, and the domain is an scFv in which VH of SEQ ID NO: 1 and VL of SEQ ID NO: 2 are linked in an order of VH, a linker peptide and VL via the linker peptide.

8. The recombinant herpes simplex virus of claim 7, wherein the linker peptide comprises an amino acid sequence of SEQ ID NO: 5.

9. The recombinant herpes simplex virus of claim 1, wherein the cancer-cell-targeting domain is a domain that recognizes and binds to CEA, which is a target molecule of a cancer cell that is a target cell, and the domain is an scFv in which VL of SEQ ID NO: 3 and VH of SEQ ID NO: 4 are linked in an order of VL, a linker peptide and VH via the linker peptide.

10. The recombinant herpes simplex virus of claim 9, wherein the linker peptide comprises an amino acid sequence of SEQ ID NO: 6.

11. The recombinant herpes simplex virus of claim 1, wherein the recombinant herpes simplex virus is configured such that arginine (R) at position 222 and phenylalanine (F) at position 223 of the amino acid sequence of gD (glycoprotein D) comprising the sequence of SEQ ID NO: 15 are substituted with asparagine (N) and isoleucine (I), respectively.

12. The recombinant herpes simplex virus of claim 1, wherein the recombinant herpes simplex virus is a recombinant HSV-1 virus, a recombinant HSV-2 virus, or an HSV-1 and HSV-2 chimeric virus.

13. The recombinant herpes simplex virus of claim 1, wherein the recombinant herpes simplex virus is recombinant HSV-1 derived from an HSV-1 KOS strain.

14. The recombinant herpes simplex virus of claim 1, further including a second expression cassette comprising a gene expressing any one selected from among (i) cytokine, (ii) chemokine, (iii) an antagonist to an immune checkpoint, (iv) a co-stimulatory factor inducing activation of an immune cell, (v) an antagonist to TGFβ inhibiting an immune response to a cancer cell, (vi) heparinase degrading heparan sulfate proteoglycan for a solid tumor microenvironment, (vii) an antagonist inhibiting a function of an angiogenic receptor VEGFR-2 (VEGF receptor-2), and (viii) a prodrug-activating enzyme converting a prodrug into a drug that is toxic to a cancer cell is further inserted into the genome of the herpes simplex virus without inhibiting proliferation of the herpes simplex virus.

15. The recombinant herpes simplex virus of claim 14, wherein the cytokine is at least one selected from among interleukins (ILs), interferons (IFNs), TNFα, GM-CSF, and G-CSF, wherein the IL is selected from the group consisting of IL-2, IL-4, IL-7, IL-10, IL-12, IL-15, IL-18, and IL-24, and wherein the IFN is selected from the group consisting of IFNα, IFNβ, and IFNγ, and the chemokine is at least one selected from among CCL2, RANTES, CCL7, CCL9, CCL10, CCL12, CCL15, CCL19, CCL21, CCL20 and XCL-1, the immune checkpoint is at least one selected from among PD-1 (programmed cell death 1), PD-L1 (programmed cell death ligand 1), PD-L2 (programmed cell death ligand 2), CD27 (cluster of differentiation 27), CD28 (cluster of differentiation 28), CD70 (cluster of differentiation 70), CD80 (cluster of differentiation 80), CD86 (cluster of differentiation 86), CD137 (cluster of differentiation 137), CD276 (cluster of differentiation 276), KIRs (killer-cell immunoglobulin-like receptors), LAG3 (lymphocyte activation gene 3), GITR (glucocorticoid-induced TNFR-related protein), GITRL (glucocorticoid-induced TNFR-related protein ligand) and CTLA-4 (cytolytic T lymphocyte associated antigen-4), the co-stimulatory factor is at least one selected from among CD2, CD7, LIGHT, NKG2C, CD27, CD28, 4-1BB, OX40, CD30, CD40, LFA-1 (lymphocyte function-associated antigen-1), ICOS (inducible T cell co-stimulator), CD3γ, CD3δ and CD3Σ, and the prodrug-activating enzyme is at least one selected from among cytosine deaminase, rat cytochrome P450 (CYP2B1), carboxylesterase, bacterial nitroreductase and PNP (purine nucleoside phosphorylase) isolated from *E. coli.*

16. The recombinant herpes simplex virus of claim 14, wherein the second expression cassette is inserted between UL3 and UL4 genes, between UL26 and UL27 genes, between UL37 and UL38 genes, between UL48 and UL49 genes, between UL53 and UL54 genes or between US1 and US2 genes in the genome of the virus, in which an insertion locus thereof is different from that of the adapter expression cassette of the fusion protein.

17. The recombinant herpes simplex virus of claim 1, wherein the fusion protein is configured in an order of $NH_2$/cancer-cell-targeting domain/extracellular domain of HVEM/COOH or extracellular domain of HVEM/cancer-cell-targeting domain.

18. The recombinant herpes simplex virus of claim 1, wherein the fusion protein is configured such that the cancer-cell-targeting domain and the extracellular domain of HVEM are linked via a linker peptide, and the fusion protein is configured in an order of $NH_2$/cancer-cell-targeting domain/linker peptide/extracellular domain of HVEM/COOH or extracellular domain of HVEM/cancer-cell-targeting domain.

* * * * *

SEQUENCE LISTING

<160> NUMBER OF SEQ ID NOS: 33

<210> SEQ ID NO 1
<211> LENGTH: 120
<212> TYPE: PRT
<213> ORGANISM: Artificial Sequence
<220> FEATURE:
<223> OTHER INFORMATION: HER2 VH

<400> SEQUENCE: 1

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser
115 120

<210> SEQ ID NO 2
<211> LENGTH: 107
<212> TYPE: PRT
<213> ORGANISM: Artificial Sequence
<220> FEATURE:
<223> OTHER INFORMATION: HER2 VL

<400> SEQUENCE: 2

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys
100 105

<210> SEQ ID NO 3
<211> LENGTH: 107
<212> TYPE: PRT
<213> ORGANISM: Artificial Sequence
<220> FEATURE:
<223> OTHER INFORMATION: CEA VH

<400> SEQUENCE: 3

Asp Ile Gln Met Thr Gln Ser Pro Ala Ser Leu Ser Ala Ser Val Gly
1 5 10 15

-continued

```
Asp Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Ala Leu Ser Glu Gly Val Pro Ser Arg Phe Ser Gly
    50                  55                  60

Ser Gly Ser Gly Thr Gln Phe Ser Leu Arg Ile Asn Ser Leu Gln Pro
65                  70                  75                  80

Glu Asp Phe Gly Asp Tyr Tyr Cys Gln His His Tyr Asn Ser Pro Tyr
                85                  90                  95

Thr Phe Gly Gly Gly Thr Lys Leu Glu Ile Lys
            100                 105


<210> SEQ ID NO 4
<211> LENGTH: 107
<212> TYPE: PRT
<213> ORGANISM: Artificial Sequence
<220> FEATURE:
<223> OTHER INFORMATION: CEA VL

<400> SEQUENCE: 4

Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Ala Leu Ser Glu Gly Val Pro Ser Arg Phe Ser Gly
    50                  55                  60

Ser Gly Ser Gly Thr Gln Phe Ser Leu Arg Ile Asn Ser Leu Gln Pro
65                  70                  75                  80

Glu Asp Phe Gly Asp Tyr Tyr Cys Gln His His Tyr Asn Ser Pro Tyr
                85                  90                  95

Thr Phe Gly Gly Gly Thr Lys Leu Glu Ile Lys
            100                 105


<210> SEQ ID NO 5
<211> LENGTH: 15
<212> TYPE: PRT
<213> ORGANISM: Artificial Sequence
<220> FEATURE:
<223> OTHER INFORMATION: HER2 Linker

<400> SEQUENCE: 5

Gly Gly Gly Gly Ser Gly Gly Gly Gly Ser Gly Gly Gly Gly Ser
1               5                   10                  15


<210> SEQ ID NO 6
<211> LENGTH: 14
<212> TYPE: PRT
<213> ORGANISM: Artificial Sequence
<220> FEATURE:
<223> OTHER INFORMATION: CEA Linker

<400> SEQUENCE: 6

Gly Ser Thr Ser Gly Ser Gly Lys Ser Ser Glu Gly Lys Gly
1               5                   10


<210> SEQ ID NO 7
<211> LENGTH: 82
```

<212> TYPE: PRT
<213> ORGANISM: Artificial Sequence
<220> FEATURE:
<223> OTHER INFORMATION: HveA 82

<400> SEQUENCE: 7

```
Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Pro Gly Thr Tyr Ile Ala His
        35                  40                  45

Leu Asn Gly Leu Ser Lys Cys Leu Gln Cys Gln Met Cys Asp Pro Ala
    50                  55                  60

Met Gly Leu Arg Ala Ser Arg Asn Cys Ser Arg Thr Glu Asn Ala Val
65                  70                  75                  80

Cys Gly
```

<210> SEQ ID NO 8
<211> LENGTH: 120
<212> TYPE: PRT
<213> ORGANISM: Artificial Sequence
<220> FEATURE:
<223> OTHER INFORMATION: Sp.-HveA 82

<400> SEQUENCE: 8

```
Met Glu Pro Pro Gly Asp Trp Gly Pro Pro Pro Trp Arg Ser Thr Pro
1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly
        115                 120
```

<210> SEQ ID NO 9
<211> LENGTH: 87
<212> TYPE: PRT
<213> ORGANISM: Artificial Sequence
<220> FEATURE:
<223> OTHER INFORMATION: HveA87

<400> SEQUENCE: 9

```
Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Pro Gly Thr Tyr Ile Ala His
        35                  40                  45

Leu Asn Gly Leu Ser Lys Cys Leu Gln Cys Gln Met Cys Asp Pro Ala
    50                  55                  60
```

```
Met Gly Leu Arg Ala Ser Arg Asn Cys Ser Arg Thr Glu Asn Ala Val
65                  70                  75                  80

Cys Gly Cys Ser Pro Gly His
                85


<210> SEQ ID NO 10
<211> LENGTH: 125
<212> TYPE: PRT
<213> ORGANISM: Artificial Sequence
<220> FEATURE:
<223> OTHER INFORMATION: Sp-HveA87

<400> SEQUENCE: 10

Met Glu Pro Pro Gly Asp Trp Gly Pro Pro Pro Trp Arg Ser Thr Pro
1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His
        115                 120                 125


<210> SEQ ID NO 11
<211> LENGTH: 102
<212> TYPE: PRT
<213> ORGANISM: Artificial Sequence
<220> FEATURE:
<223> OTHER INFORMATION: HveA102

<400> SEQUENCE: 11

Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Pro Gly Thr Tyr Ile Ala His
        35                  40                  45

Leu Asn Gly Leu Ser Lys Cys Leu Gln Cys Gln Met Cys Asp Pro Ala
    50                  55                  60

Met Gly Leu Arg Ala Ser Arg Asn Cys Ser Arg Thr Glu Asn Ala Val
65                  70                  75                  80

Cys Gly Cys Ser Pro Gly His Phe Cys Ile Val Gln Asp Gly Asp His
                85                  90                  95

Cys Ala Ala Cys Arg Ala
            100


<210> SEQ ID NO 12
<211> LENGTH: 140
<212> TYPE: PRT
<213> ORGANISM: Artificial Sequence
<220> FEATURE:
<223> OTHER INFORMATION: Sp-HveA102
```

-continued

<400> SEQUENCE: 12

Met Glu Pro Pro Gly Asp Trp Gly Pro Pro Pro Trp Arg Ser Thr Pro
1 5 10 15

Arg Thr Asp Val Leu Arg Leu Val Leu Tyr Leu Thr Phe Leu Gly Ala
20 25 30

Pro Cys Tyr Ala Pro Ala Leu Pro Ser Cys Lys Glu Asp Glu Tyr Pro
35 40 45

Val Gly Ser Glu Cys Cys Pro Lys Cys Ser Pro Gly Tyr Arg Val Lys
50 55 60

Glu Ala Cys Gly Glu Leu Thr Gly Thr Val Cys Glu Pro Cys Pro Pro
65 70 75 80

Gly Thr Tyr Ile Ala His Leu Asn Gly Leu Ser Lys Cys Leu Gln Cys
85 90 95

Gln Met Cys Asp Pro Ala Met Gly Leu Arg Ala Ser Arg Asn Cys Ser
100 105 110

Arg Thr Glu Asn Ala Val Cys Gly Cys Ser Pro Gly His Phe Cys Ile
115 120 125

Val Gln Asp Gly Asp His Cys Ala Ala Cys Arg Ala
130 135 140

<210> SEQ ID NO 13
<211> LENGTH: 107
<212> TYPE: PRT
<213> ORGANISM: Artificial Sequence
<220> FEATURE:
<223> OTHER INFORMATION: HveA107

<400> SEQUENCE: 13

Leu Pro Ser Cys Lys Glu Asp Glu Tyr Pro Val Gly Ser Glu Cys Cys
1 5 10 15

Pro Lys Cys Ser Pro Gly Tyr Arg Val Lys Glu Ala Cys Gly Glu Leu
20 25 30

Thr Gly Thr Val Cys Glu Pro Cys Pro Pro Gly Thr Tyr Ile Ala His
35 40 45

Leu Asn Gly Leu Ser Lys Cys Leu Gln Cys Gln Met Cys Asp Pro Ala
50 55 60

Met Gly Leu Arg Ala Ser Arg Asn Cys Ser Arg Thr Glu Asn Ala Val
65 70 75 80

Cys Gly Cys Ser Pro Gly His Phe Cys Ile Val Gln Asp Gly Asp His
85 90 95

Cys Ala Ala Cys Arg Ala Tyr Ala Thr Ser Ser
100 105

<210> SEQ ID NO 14
<211> LENGTH: 145
<212> TYPE: PRT
<213> ORGANISM: Artificial Sequence
<220> FEATURE:
<223> OTHER INFORMATION: Sp-HveA107

<400> SEQUENCE: 14

Met Glu Pro Pro Gly Asp Trp Gly Pro Pro Pro Trp Arg Ser Thr Pro
1 5 10 15

Arg Thr Asp Val Leu Arg Leu Val Leu Tyr Leu Thr Phe Leu Gly Ala
20 25 30

Pro Cys Tyr Ala Pro Ala Leu Pro Ser Cys Lys Glu Asp Glu Tyr Pro
35 40 45

```
Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser
145


<210> SEQ ID NO 15
<211> LENGTH: 369
<212> TYPE: PRT
<213> ORGANISM: Artificial Sequence
<220> FEATURE:
<223> OTHER INFORMATION: gD ASM47818

<400> SEQUENCE: 15

Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Thr Asp Pro Pro
            20                  25                  30

Gly Val Arg Arg Val Tyr His Ile Gln Ala Gly Leu Pro Asp Pro Phe
        35                  40                  45

Gln Pro Pro Ser Leu Pro Ile Thr Val Tyr Tyr Ala Val Leu Glu Arg
    50                  55                  60

Ala Cys Arg Ser Val Leu Leu Asn Ala Pro Ser Glu Ala Pro Gln Ile
65                  70                  75                  80

Val Arg Gly Ala Ser Glu Asp Val Arg Lys Gln Pro Tyr Asn Leu Thr
                85                  90                  95

Ile Ala Trp Phe Arg Met Gly Gly Asn Cys Ala Ile Pro Ile Thr Val
            100                 105                 110

Met Glu Tyr Thr Glu Cys Ser Tyr Asn Lys Ser Leu Gly Ala Cys Pro
        115                 120                 125

Ile Arg Thr Gln Pro Arg Trp Asn Tyr Tyr Asp Ser Phe Ser Ala Val
    130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Lys Gly Ser Cys Lys Tyr Ala
            180                 185                 190

Leu Pro Leu Arg Ile Pro Pro Ser Ala Cys Leu Ser Pro Gln Ala Tyr
        195                 200                 205

Gln Gln Gly Val Thr Val Asp Ser Ile Gly Met Leu Pro Arg Phe Ile
    210                 215                 220

Pro Glu Asn Gln Arg Thr Val Ala Val Tyr Ser Leu Lys Ile Ala Gly
225                 230                 235                 240

Trp His Gly Pro Lys Ala Pro Tyr Thr Ser Thr Leu Leu Pro Pro Glu
                245                 250                 255
```

```
Leu Ser Glu Thr Pro Asn Ala Thr Gln Pro Glu Leu Ala Pro Glu Asp
            260                 265                 270

Pro Glu Asp Ser Ala Leu Leu Glu Asp Pro Val Gly Thr Val Ala Pro
        275                 280                 285

Gln Ile Pro Pro Asn Trp His Ile Pro Ser Ile Gln Asp Ala Ala Thr
    290                 295                 300

Pro Tyr His Pro Pro Ala Thr Pro Asn Asn Met Gly Leu Ile Ala Gly
305                 310                 315                 320

Ala Val Gly Gly Ser Leu Leu Ala Ala Leu Val Ile Cys Gly Ile Val
                325                 330                 335

Tyr Trp Met His Arg Arg Thr Arg Lys Ala Pro Lys Arg Ile Arg Leu
            340                 345                 350

Pro His Ile Arg Glu Asp Asp Gln Pro Ser Ser His Gln Pro Leu Phe
        355                 360                 365

Tyr


<210> SEQ ID NO 16
<211> LENGTH: 60
<212> TYPE: DNA
<213> ORGANISM: Artificial Sequence
<220> FEATURE:
<223> OTHER INFORMATION: gD-rpsL For

<400> SEQUENCE: 16

cccaggccta ccagcagggg gtgacggtgg acagcatcgg gatgctgccc ggcctggtga     60


<210> SEQ ID NO 17
<211> LENGTH: 88
<212> TYPE: DNA
<213> ORGANISM: Artificial Sequence
<220> FEATURE:
<223> OTHER INFORMATION: gD-rpsL Rev

<400> SEQUENCE: 17

ccggcgatct tcaagctgta tacggcgacg gtgcgctggt tctcggggat tcagaagaac     60

tcgtcaagaa ggcgtgatgg cgggatcg                                        88


<210> SEQ ID NO 18
<211> LENGTH: 369
<212> TYPE: PRT
<213> ORGANISM: Artificial Sequence
<220> FEATURE:
<223> OTHER INFORMATION: gD R222N_F223I

<400> SEQUENCE: 18

Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Thr Asp Pro Pro
            20                  25                  30

Gly Val Arg Arg Val Tyr His Ile Gln Ala Gly Leu Pro Asp Pro Phe
        35                  40                  45

Gln Pro Pro Ser Leu Pro Ile Thr Val Tyr Tyr Ala Val Leu Glu Arg
    50                  55                  60

Ala Cys Arg Ser Val Leu Leu Asn Ala Pro Ser Glu Ala Pro Gln Ile
65                  70                  75                  80

Val Arg Gly Ala Ser Glu Asp Val Arg Lys Gln Pro Tyr Asn Leu Thr
                85                  90                  95

Ile Ala Trp Phe Arg Met Gly Gly Asn Cys Ala Ile Pro Ile Thr Val
```

-continued

```
            100                 105                 110

Met Glu Tyr Thr Glu Cys Ser Tyr Asn Lys Ser Leu Gly Ala Cys Pro
        115                 120                 125

Ile Arg Thr Gln Pro Arg Trp Asn Tyr Tyr Asp Ser Phe Ser Ala Val
    130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Lys Gly Ser Cys Lys Tyr Ala
            180                 185                 190

Leu Pro Leu Arg Ile Pro Pro Ser Ala Cys Leu Ser Pro Gln Ala Tyr
        195                 200                 205

Gln Gln Gly Val Thr Val Asp Ser Ile Gly Met Leu Pro Asn Ile Ile
    210                 215                 220

Pro Glu Asn Gln Arg Thr Val Ala Val Tyr Ser Leu Lys Ile Ala Gly
225                 230                 235                 240

Trp His Gly Pro Lys Ala Pro Tyr Thr Ser Thr Leu Leu Pro Pro Glu
                245                 250                 255

Leu Ser Glu Thr Pro Asn Ala Thr Gln Pro Glu Leu Ala Pro Glu Asp
            260                 265                 270

Pro Glu Asp Ser Ala Leu Leu Glu Asp Pro Val Gly Thr Val Ala Pro
        275                 280                 285

Gln Ile Pro Pro Asn Trp His Ile Pro Ser Ile Gln Asp Ala Ala Thr
    290                 295                 300

Pro Tyr His Pro Pro Ala Thr Pro Asn Asn Met Gly Leu Ile Ala Gly
305                 310                 315                 320

Ala Val Gly Gly Ser Leu Leu Ala Ala Leu Val Ile Cys Gly Ile Val
                325                 330                 335

Tyr Trp Met His Arg Arg Thr Arg Lys Ala Pro Lys Arg Ile Arg Leu
            340                 345                 350

Pro His Ile Arg Glu Asp Asp Gln Pro Ser Ser His Gln Pro Leu Phe
        355                 360                 365

Tyr
```

<210> SEQ ID NO 19
<211> LENGTH: 74
<212> TYPE: DNA
<213> ORGANISM: Artificial Sequence
<220> FEATURE:
<223> OTHER INFORMATION: UL26/27-rpsL_For

<400> SEQUENCE: 19

```
gcgtgggggg gaggaaatcg gcactgacca agggggtccg ttttgtcacg tcagaagaac     60

tcgtcaagaa ggcg                                                       74
```

<210> SEQ ID NO 20
<211> LENGTH: 74
<212> TYPE: DNA
<213> ORGANISM: Artificial Sequence
<220> FEATURE:
<223> OTHER INFORMATION: UL26/27-rpsL_Rev

<400> SEQUENCE: 20

```
aacacataaa ctcccccggg tgtccgcggc ctgtttcctc tttcctttcc ggcctggtga     60

tgatggcggg atcg                                                       74
```

<210> SEQ ID NO 21
<211> LENGTH: 74
<212> TYPE: DNA
<213> ORGANISM: Artificial Sequence
<220> FEATURE:
<223> OTHER INFORMATION: UL26-tkpA_For

<400> SEQUENCE: 21
gcgtgggggg gaggaaatcg gcactgacca agggggtccg ttttgtcacg gcctcagaag 60
ccatagagcc cacc 74

<210> SEQ ID NO 22
<211> LENGTH: 74
<212> TYPE: DNA
<213> ORGANISM: Artificial Sequence
<220> FEATURE:
<223> OTHER INFORMATION: UL27-pCMV_Rev

<400> SEQUENCE: 22
aacacataaa ctcccccggg tgtccgcggc ctgtttcctc tttcctttcc tatacgcgtt 60
gacattgatt attg 74

<210> SEQ ID NO 23
<211> LENGTH: 351
<212> TYPE: PRT
<213> ORGANISM: Artificial Sequence
<220> FEATURE:
<223> OTHER INFORMATION: HER2scFv-HveA adaptor

<400> SEQUENCE: 23

Met Ser Val Pro Thr Gln Val Leu Gly Leu Leu Leu Leu Trp Leu Thr
1 5 10 15

Gly Ala Arg Cys Glu Val Gln Leu Val Glu Ser Gly Gly Gly Leu Val
20 25 30

Gln Pro Gly Gly Ser Leu Arg Leu Ser Cys Ala Ala Ser Gly Phe Asn
35 40 45

Ile Lys Asp Thr Tyr Ile His Trp Val Arg Gln Ala Pro Gly Lys Gly
50 55 60

Leu Glu Trp Val Ala Arg Ile Tyr Pro Thr Asn Gly Tyr Thr Arg Tyr
65 70 75 80

Ala Asp Ser Val Lys Gly Arg Phe Thr Ile Ser Ala Asp Thr Ser Lys
85 90 95

Asn Thr Ala Tyr Leu Gln Met Asn Ser Leu Arg Ala Glu Asp Thr Ala
100 105 110

Val Tyr Tyr Cys Ser Arg Trp Gly Gly Asp Gly Phe Tyr Ala Met Asp
115 120 125

Tyr Trp Gly Gln Gly Thr Leu Val Thr Val Ser Ser Gly Gly Gly Gly
130 135 140

Ser Gly Gly Gly Gly Ser Gly Gly Gly Gly Ser Asp Ile Gln Met Thr
145 150 155 160

Gln Ser Pro Ser Ser Leu Ser Ala Ser Val Gly Asp Arg Val Thr Ile
165 170 175

Thr Cys Arg Ala Ser Gln Asp Val Asn Thr Ala Val Ala Trp Tyr Gln
180 185 190

Gln Lys Pro Gly Lys Ala Pro Lys Leu Leu Ile Tyr Ser Ala Ser Phe
195 200 205

Leu Tyr Ser Gly Val Pro Ser Arg Phe Ser Gly Ser Arg Ser Gly Thr

-continued

```
    210                 215                 220

Asp Phe Thr Leu Thr Ile Ser Ser Leu Gln Pro Glu Asp Phe Ala Thr
225                 230                 235                 240

Tyr Tyr Cys Gln Gln His Tyr Thr Thr Pro Pro Thr Phe Gly Gln Gly
                245                 250                 255

Thr Lys Val Glu Ile Lys Gly Gly Gly Gly Ser Glu Phe Leu Pro Ser
            260                 265                 270

Cys Lys Glu Asp Glu Tyr Pro Val Gly Ser Glu Cys Cys Pro Lys Cys
        275                 280                 285

Ser Pro Gly Tyr Arg Val Lys Glu Ala Cys Gly Glu Leu Thr Gly Thr
    290                 295                 300

Val Cys Glu Pro Cys Pro Pro Gly Thr Tyr Ile Ala His Leu Asn Gly
305                 310                 315                 320

Leu Ser Lys Cys Leu Gln Cys Gln Met Cys Asp Pro Ala Met Gly Leu
                325                 330                 335

Arg Ala Ser Arg Asn Cys Ser Arg Thr Glu Asn Ala Val Cys Gly
            340                 345                 350


<210> SEQ ID NO 24
<211> LENGTH: 1053
<212> TYPE: DNA
<213> ORGANISM: Artificial Sequence
<220> FEATURE:
<223> OTHER INFORMATION: HER2scFv-HveA adaptor

<400> SEQUENCE: 24

atgagtgtgc ccactcaggt cctggggttg ctgctgctgt ggcttacagg tgccagatgt     60

gaggtgcagc tggttgaatc tggcggagga ctggttcagc ctggcggatc tctgagactg    120

tcttgtgccg ccagcggctt caacatcaag gacacctaca tccactgggt ccgacaggcc    180

cctggcaaag gacttgaatg ggtcgccaga atctacccca ccaacggcta caccagatac    240

gccgactctg tgaagggcag attcaccatc agcgccgaca ccagcaagaa caccgcctac    300

ctgcagatga acagcctgag agccgaggac accgccgtgt actactgttc tagatgggga    360

ggcgacggct tctacgccat ggattattgg ggccagggca ccctggtcac agtttctagc    420

ggaggcggag gttctggcgg cggaggaagt ggtggcggag gctctgatat ccagatgaca    480

cagagcccca gcagcctgtc tgcctctgtg ggagacagag tgaccatcac ctgtagagcc    540

agccaggacg tgaacacagc cgtggcttgg tatcagcaga agcctggcaa ggcccctaag    600

ctgctgatct acagcgccag ctttctgtac agcggcgtgc ccagcagatt cagcggctct    660

agaagcggca ccgacttcac cctgaccata agcagtctgc agcccgagga cttcgccacc    720

tactactgtc agcagcacta caccacacct ccaaccttcg gacagggcac caaggtggaa    780

atcaagggtg gtggcggttc agaattcctg ccgtcctgca aggaggacga gtacccagtg    840

ggctccgagt gctgccccaa gtgcagtcca ggttatcgtg tgaaggaggc ctgcggggag    900

ctgacgggca cagtgtgtga accctgccct ccaggcacct acattgccca cctcaatggc    960

ctaagcaagt gtctgcagtg ccaaatgtgt gacccagcca tgggcctgcg cgcgagccgg   1020

aactgctcca ggacagagaa cgccgtgtgt ggc                                1053


<210> SEQ ID NO 25
<211> LENGTH: 369
<212> TYPE: PRT
<213> ORGANISM: Artificial Sequence
<220> FEATURE:
<223> OTHER INFORMATION: HveA-HER2scFv adaptor
```

-continued

<400> SEQUENCE: 25

```
Met Glu Pro Pro Gly Asp Trp Gly Pro Pro Pro Trp Arg Ser Thr Pro
1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Gly Gly Gly Gly Ser Gly Ser Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Gly Gly Gly Gly Ser Asp Ile Gln Met Thr Gln Ser Pro Ser Ser
            260                 265                 270

Leu Ser Ala Ser Val Gly Asp Arg Val Thr Ile Thr Cys Arg Ala Ser
        275                 280                 285

Gln Asp Val Asn Thr Ala Val Ala Trp Tyr Gln Gln Lys Pro Gly Lys
    290                 295                 300

Ala Pro Lys Leu Leu Ile Tyr Ser Ala Ser Phe Leu Tyr Ser Gly Val
305                 310                 315                 320

Pro Ser Arg Phe Ser Gly Ser Arg Ser Gly Thr Asp Phe Thr Leu Thr
                325                 330                 335

Ile Ser Ser Leu Gln Pro Glu Asp Phe Ala Thr Tyr Tyr Cys Gln Gln
            340                 345                 350

His Tyr Thr Thr Pro Pro Thr Phe Gly Gln Gly Thr Lys Val Glu Ile
        355                 360                 365

Lys
```

<210> SEQ ID NO 26
<211> LENGTH: 1107
<212> TYPE: DNA
<213> ORGANISM: Artificial Sequence -continued
<220> FEATURE:
<223> OTHER INFORMATION: HveA-HER2scFv adaptor

<400> SEQUENCE: 26

```
atggagcctc ctggagactg gggcctcct ccctggagat ccacccccag aaccgacgtc      60

ttgaggctgg tgctgtatct caccttcctg ggagcccct gctacgcccc agctctgccg     120

tcctgcaagg aggacgagta cccagtgggc tccgagtgct gccccaagtg cagtccaggt     180

tatcgtgtga aggaggcctg cggggagctg acgggcacag tgtgtgaacc ctgccctcca     240

ggcacctaca ttgcccacct caatggccta agcaagtgtc tgcagtgcca aatgtgtgac     300

ccagccatgg gcctgcgcgc gagccggaac tgctccagga cagagaacgc cgtgtgtggc     360

ggtggtggcg gttcaggatc cgaggtgcag ctggttgaat ctggcggagg actggttcag     420

cctggcggat ctctgagact gtcttgtgcc gccagcggct tcaacatcaa ggacacctac     480

atccactggg tccgacaggc ccctggcaaa ggacttgaat gggtcgccag aatctacccc     540

accaacggct acaccagata cgccgactct gtgaagggca gattcaccat cagcgccgac     600

accagcaaga acaccgccta cctgcagatg aacagcctga gagccgagga caccgccgtg     660

tactactgtt ctagatgggg aggcgacggc ttctacgcca tggattattg gggccagggc     720

accctggtca cagtttctag cggaggcgga ggttctggcg gcggaggaag tggtggcgga     780

ggctctgata tccagatgac acagagcccc agcagcctgt ctgcctctgt gggagacaga     840

gtgaccatca cctgtagagc cagccaggac gtgaacacag ccgtggcttg gtatcagcag     900

aagcctggca aggcccctaa gctgctgatc tacagcgcca gctttctgta cagcggcgtg     960

cccagcagat tcagcggctc tagaagcggc accgacttca ccctgaccat aagcagtctg    1020

cagcccgagg acttcgccac ctactactgt cagcagcact acaccacacc tccaaccttc    1080

ggacagggca ccaaggtgga aatcaag                                        1107
```

<210> SEQ ID NO 27
<211> LENGTH: 346
<212> TYPE: PRT
<213> ORGANISM: Artificial Sequence
<220> FEATURE:
<223> OTHER INFORMATION: CEAscFv-HveA

<400> SEQUENCE: 27

```
Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Asp Thr Val Thr Ile Thr Cys Arg Ala Ser Glu Asn
        35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Ala Leu Ser Glu Gly Val Pro Ser
65                  70                  75                  80

Arg Phe Ser Gly Ser Gly Ser Gly Thr Gln Phe Ser Leu Arg Ile Asn
                85                  90                  95

Ser Leu Gln Pro Glu Asp Phe Gly Asp Tyr Tyr Cys Gln His His Tyr
            100                 105                 110

Asn Ser Pro Tyr Thr Phe Gly Gly Gly Thr Lys Leu Glu Ile Lys Gly
        115                 120                 125

Ser Thr Ser Gly Ser Gly Lys Ser Ser Glu Gly Lys Gly Gln Ile Gln
    130                 135                 140
```

```
Leu Val Gln Ser Gly Pro Glu Leu Lys Lys Pro Gly Glu Thr Val Lys
145                 150                 155                 160

Ile Ser Cys Lys Ala Ser Gly Tyr Ser Phe Thr Asn Asp Gly Ile Asn
                165                 170                 175

Trp Val Lys Gln Ala Pro Gly Lys Gly Phe Lys Tyr Met Gly Trp Ile
            180                 185                 190

Asn Thr Ile Thr Gly Glu Pro Thr Tyr Thr Glu Asp Phe Lys Gly Arg
        195                 200                 205

Phe Ala Phe Ser Leu Glu Thr Ser Ala Ser Thr Ala Tyr Leu Gln Ile
    210                 215                 220

Asn Asn Leu Lys Asp Glu Asp Thr Ala Thr Phe Phe Cys Ala Lys Gly
225                 230                 235                 240

Thr Gly Thr Ser Ala Tyr Trp Gly Gln Gly Thr Leu Val Thr Val Ser
                245                 250                 255

Ala Gly Gly Gly Gly Ser Glu Phe Leu Pro Ser Cys Lys Glu Asp Glu
            260                 265                 270

Tyr Pro Val Gly Ser Glu Cys Cys Pro Lys Cys Ser Pro Gly Tyr Arg
        275                 280                 285

Val Lys Glu Ala Cys Gly Glu Leu Thr Gly Thr Val Cys Glu Pro Cys
    290                 295                 300

Pro Pro Gly Thr Tyr Ile Ala His Leu Asn Gly Leu Ser Lys Cys Leu
305                 310                 315                 320

Gln Cys Gln Met Cys Asp Pro Ala Met Gly Leu Arg Ala Ser Arg Asn
                325                 330                 335

Cys Ser Arg Thr Glu Asn Ala Val Cys Gly
            340                 345
```

<210> SEQ ID NO 28
<211> LENGTH: 1038
<212> TYPE: DNA
<213> ORGANISM: Artificial Sequence
<220> FEATURE:
<223> OTHER INFORMATION: CEAscFv-HveA adaptor

<400> SEQUENCE: 28

```
atgagtgtgc ccactcaggt cctggggttg ctgctgctgt ggcttacagg tgccagatgt      60

gacatccaga tgactcagtc tccagcctcc ctttctgcat ctgtgggaga cactgtcacc     120

atcacatgtc gagcaagtga gaacatttat agttatttag catggtatca gcagaaacag     180

ggaaaatctc ctcagctcct ggtctataat gcaaaggcct tatcagaagg tgtgccgtca     240

aggttcagtg gcagtggatc aggcacacag ttttctctga ggatcaacag cctgcagcct     300

gaagattttg ggattatta ctgtcaacat cattataatt ctccttatac gttcggaggg     360

gggaccaaac tggaaataaa gggctccacc tccgggtctg gtaaatcttc cgagggcaag     420

ggccagatcc agttggtgca gtctggacct gagctgaaga agcctggaga gacagtcaag     480

atctcctgca aggcttctgg ttattccttc acaaacgatg gaataaactg ggtgaagcag     540

gctccaggaa agggttttaa gtacatgggc tggataaaca ccatcactgg agagccaaca     600

tatactgaag acttcaaggg gcggtttgcc ttctctttgg aaacctctgc cagcactgcc     660

tatttgcaga tcaacaacct caaagatgag gacacggcta catttttctg tgcaaagggg     720

actgggacga gcgcttactg gggccaaggg actctggtca ctgtctctgc tggtggtggc     780

ggttcagaat tcctgccgtc ctgcaaggag gacgagtacc cagtgggctc cgagtgctgc     840

cccaagtgca gtccaggtta tcgtgtgaag gaggcctgcg gggagctgac gggcacagtg     900
```

tgtgaaccct gccctccagg cacctacatt gcccacctca atggcctaag caagtgtctg 960
cagtgccaaa tgtgtgaccc agccatgggc ctgcgcgcga gccggaactg ctccaggaca 1020
gagaacgccg tgtgtggc 1038

<210> SEQ ID NO 29
<211> LENGTH: 79
<212> TYPE: DNA
<213> ORGANISM: Artificial Sequence
<220> FEATURE:
<223> OTHER INFORMATION: HSV-1_UL3/4-rpsL-neo_for

<400> SEQUENCE: 29
taaataacac ataaatttgg ctggttgttt gttgtcttta atggaccgcc cgcaaggcct 60
ggtgatgatg gcgggatcg 79

<210> SEQ ID NO 30
<211> LENGTH: 78
<212> TYPE: DNA
<213> ORGANISM: Artificial Sequence
<220> FEATURE:
<223> OTHER INFORMATION: HSV-1_UL3/4-rpsL-neo_rev

<400> SEQUENCE: 30
taggatcccg gccggatcgc gctcgtcacc cgacactgaa acgccccccc cccctcagaa 60
gaactcgtca agaaggcg 78

<210> SEQ ID NO 31
<211> LENGTH: 79
<212> TYPE: DNA
<213> ORGANISM: Artificial Sequence
<220> FEATURE:
<223> OTHER INFORMATION: HSV-1_UL3/4-HM_pCMV_For

<400> SEQUENCE: 31
taaataacac ataaatttgg ctggttgttt gttgtcttta atggaccgcc cgcaatatac 60
gcgttgacat tgattattg 79

<210> SEQ ID NO 32
<211> LENGTH: 78
<212> TYPE: DNA
<213> ORGANISM: Artificial Sequence
<220> FEATURE:
<223> OTHER INFORMATION: UL3/4_bGH_poly_Rev

<400> SEQUENCE: 32
taggatcccg gccggatcgc gctcgtcacc cgacactgaa acgccccccc ccccgcctca 60
gaagccatag agcccacc 78

<210> SEQ ID NO 33
<211> LENGTH: 20
<212> TYPE: PRT
<213> ORGANISM: Artificial Sequence
<220> FEATURE:
<223> OTHER INFORMATION: Signal seq. HER2

<400> SEQUENCE: 33

Met Ser Val Pro Thr Gln Val Leu Gly Leu Leu Leu Leu Trp Leu Thr
1 5 10 15

Gly Ala Arg Cys
20